US007537560B2

(12) United States Patent
Powers et al.

(10) Patent No.: US 7,537,560 B2
(45) Date of Patent: May 26, 2009

(54) CONTAINMENT, SHIELDING, INFORMATION DISPLAY, DISTRIBUTION AND ADMINISTRATION OF RADIOACTIVE PHARMACEUTICALS

(75) Inventors: Donald L. Powers, Oakdale, TN (US); Henry M Chilton, Oak Ridge, TN (US); Craig H. Fischer, Knoxville, TN (US)

(73) Assignee: Don Powers, Oakdale, TN (US)

( * ) Notice: Subject to any disclaimer, the term of this patent is extended or adjusted under 35 U.S.C. 154(b) by 609 days.

(21) Appl. No.: 10/947,681

(22) Filed: Sep. 23, 2004

(65) Prior Publication Data

US 2005/0107698 A1 May 19, 2005

Related U.S. Application Data

(60) Provisional application No. 60/507,311, filed on Sep. 30, 2003.

(51) Int. Cl.
*A61N 5/00* (2006.01)

(52) U.S. Cl. ............................................... 600/5; 600/1

(58) Field of Classification Search ................. 600/1–8; 29/469; 250/370.1, 506.1, 370, 505.1, 507.1, 250/496.1; 141/1, 311 R; 206/365
See application file for complete search history.

(56) References Cited

U.S. PATENT DOCUMENTS 3,673,411 A * 6/1972 Glasser .................... 250/506.1
4,084,097 A 4/1978 Czaplinski et al.
4,401,108 A 8/1983 Galkin et al.
4,642,463 A 2/1987 Thomas
4,846,235 A 7/1989 Handke
4,869,299 A 9/1989 Handke
5,147,282 A 9/1992 Kan
5,274,239 A 12/1993 Lane et al.
6,159,141 A 12/2000 Apple et al.
6,162,165 A 12/2000 Apple et al.
6,267,717 B1 7/2001 Stoll et al.
6,425,174 B1 7/2002 Reich
6,586,758 B2 * 7/2003 Martin .................... 250/515.1
7,086,133 B2 * 8/2006 Reich ........................ 29/426.3
2003/0222228 A1 * 12/2003 Chen Fu et al. .......... 250/507.1

* cited by examiner

*Primary Examiner*—Charles A Marmor, II
*Assistant Examiner*—Christine D Hopkins
(74) *Attorney, Agent, or Firm*—Luedeka, Neely & Graham, P.C.

(57) ABSTRACT

A shielded radioactive medical apparatus has a tubular housing with a quick release cap configured for closing an open end of the tubular housing. A quick release mechanism holds the quick release cap on an open end of the tubular housing. A data display module on the housing communicates with an outside computer for receiving and transmitting information. The data display model also calculates and displays the radioactivity of a dose within the housing.

5 Claims, 26 Drawing Sheets

CONTAINMENT, SHIELDING, INFORMATION DISPLAY, DISTRIBUTION AND ADMINISTRATION OF RADIOACTIVE PHARMACEUTICALS

This is a utility patent application claiming priority to Provisional Application Ser. No. 60/507,311 filed Sep. 30, 2003, the teachings of which are incorporated herein.

FIELD OF INVENTION

The present invention relates to the field of radioactive pharmaceuticals, and particularly relates to a medical apparatus for delivering radioactive pharmaceuticals.

SUMMARY OF INVENTION

In accordance with the present invention, a shielded radioactive medical apparatus is provided for delivering medical treatments in the form of radioactive objects. A tubular housing has a closed end and an open end. A quick release cap is configured for closing the open end of the tubular housing and a quick release mechanism engages and holds the cap on the open end. Preferably, a radioactive shield is located within the tubular housing and within the quick release cap.

In the one embodiment, the medical apparatus may include a data display module associated with the housing and capable of communicating with an outside computer system. Typically, the data display module will include an internal power supply, a data processing unit, a memory, a user input and a display. A communications port may also be provided for communicating with a computer. The data display module may receive from an outside computer system the radioactivity of a dose contained within the apparatus. The data display module then continuously calculates the radioactivity of the dose as it declines and displays the radioactivity of the dose. In addition, other information may be stored within the data display module for informing the health care providers as desired.

BRIEF DESCRIPTION OF THE DRAWINGS

Advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
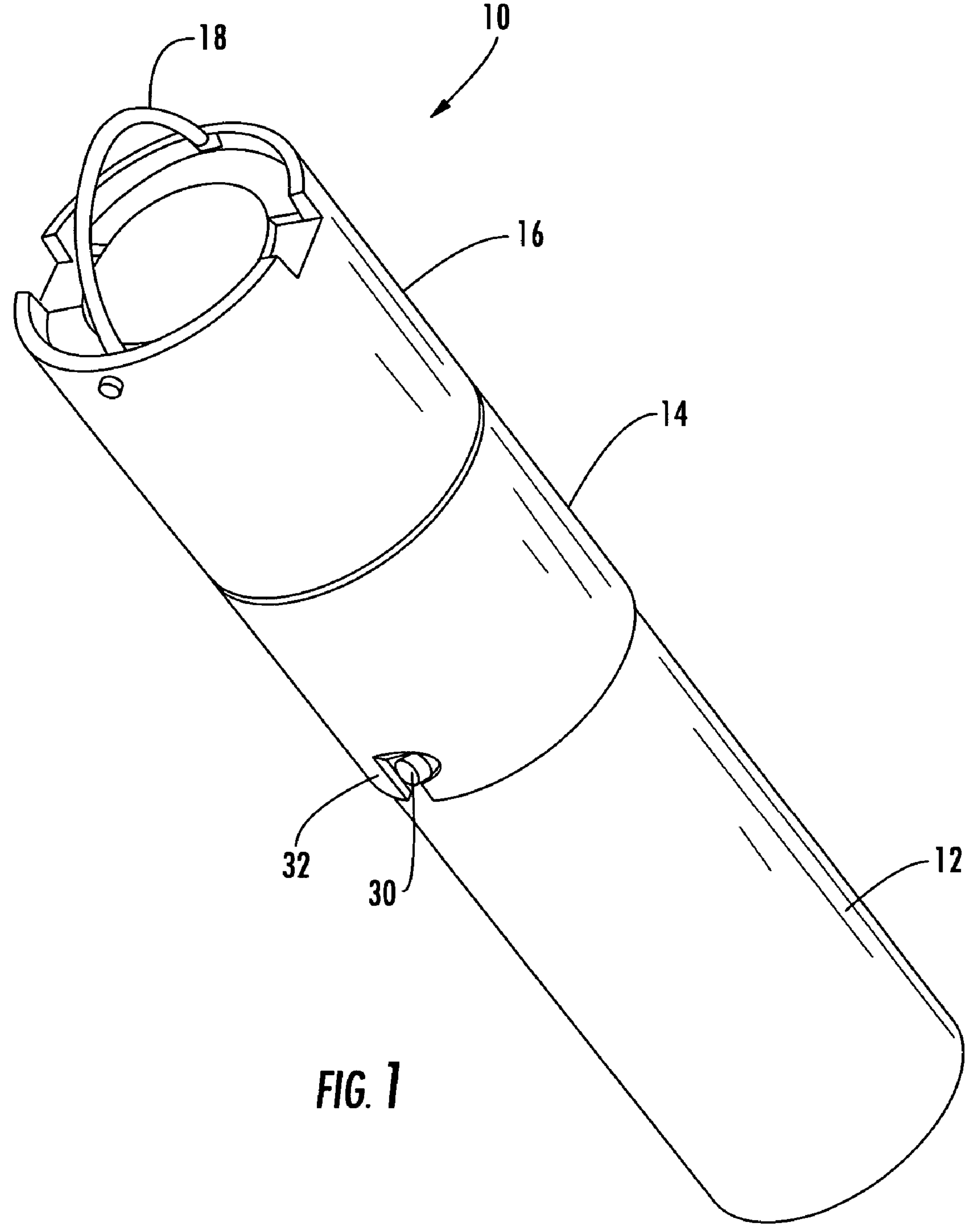
FIG. 1 is a view of the shielded radioactive medical container according to a preferred embodiment of the invention.

FIG. 1 illustrates a shielded radioactive medical container 10 for holding radioactive objects, most preferably a shielded syringe containing a radioactive solution, which allows a user to be exposed to a minimum amount of radiation. The shielded container 10 includes a housing 12, a quick release cap 16, a handle 18, and a collar 14. In a preferred embodiment, the container 10 is tubular to allow convenient handling and storage, and in a most preferred embodiment is cylindrical. A syringe, or other radioactive material, may be placed into the tubular housing for storage and transportation, and when the quick release cap 16 is secured in place, radiation will be contained and exposure measured at the external surface of the container 10 will be minimized. The container 10 is preferably dimensioned so that a single syringe will fit inside. However, the container 10 may be of any dimension, including dimensioned to fit all sized syringes, a plurality of syringes, or other objects.

Figure 2:
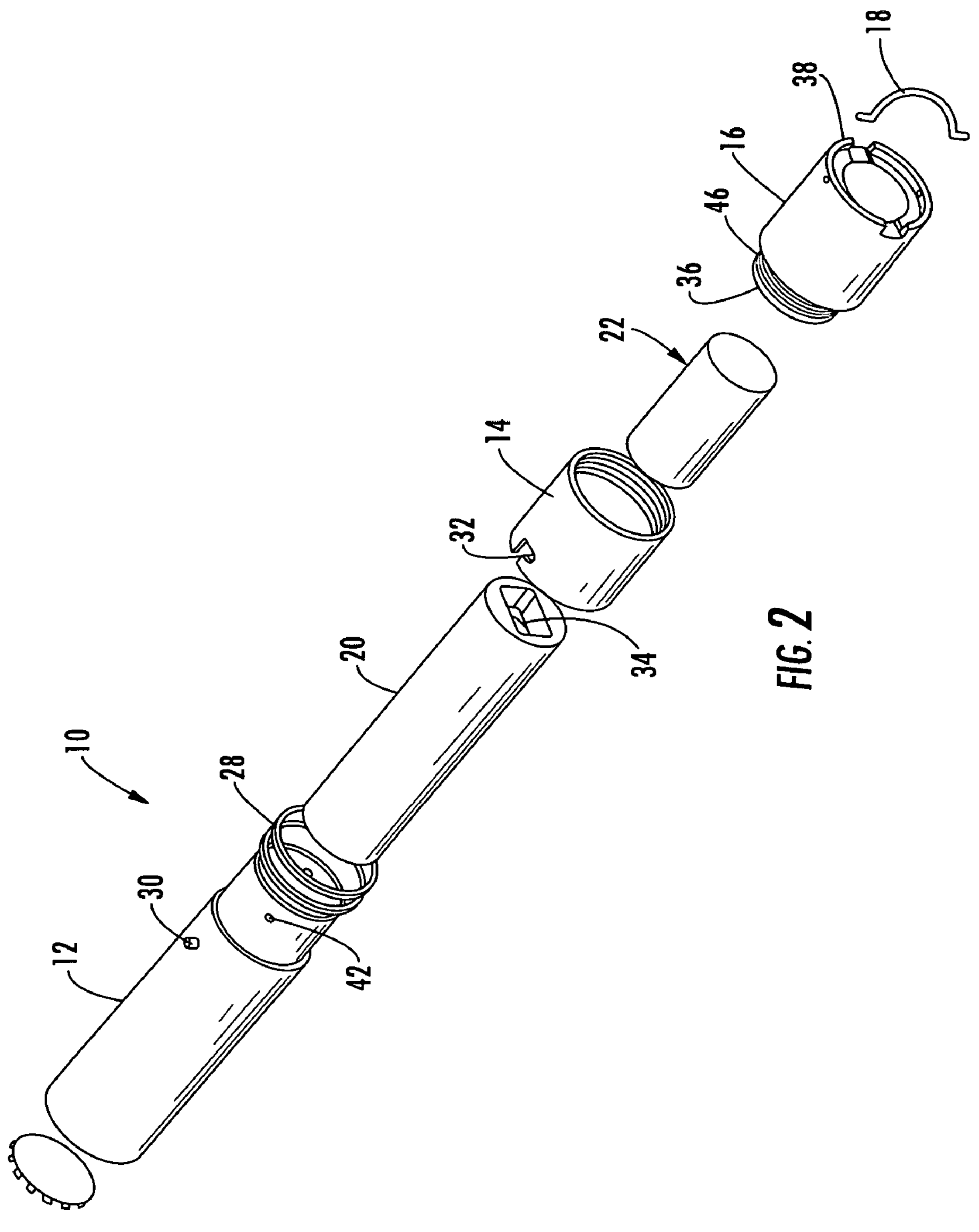
FIG. 2 is an exploded view of the shielded radioactive medical container according to a preferred embodiment of the invention.
Figure 5A:
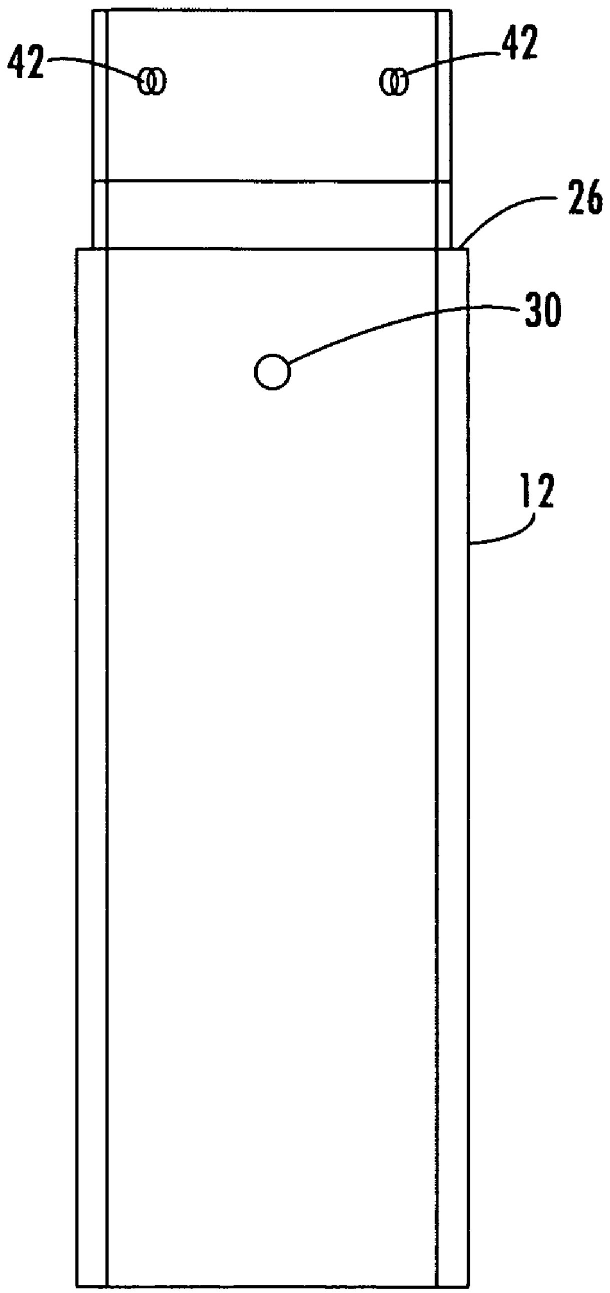
FIGS. 5*a-b* are views of the housing of the shielded radioactive medical container according to a preferred embodiment of the invention.
Figure 5B:
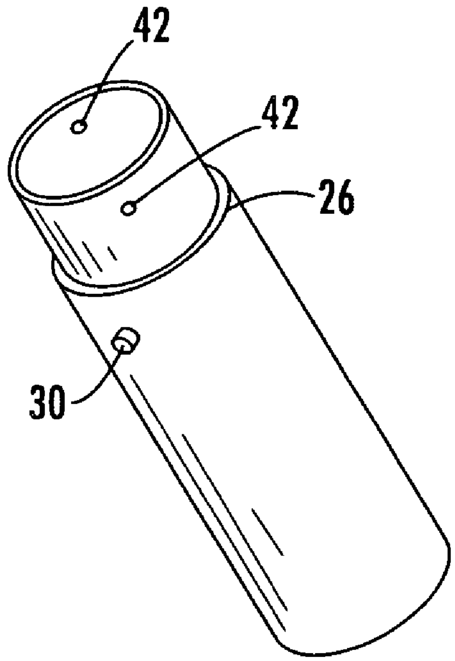
Figure 6A:
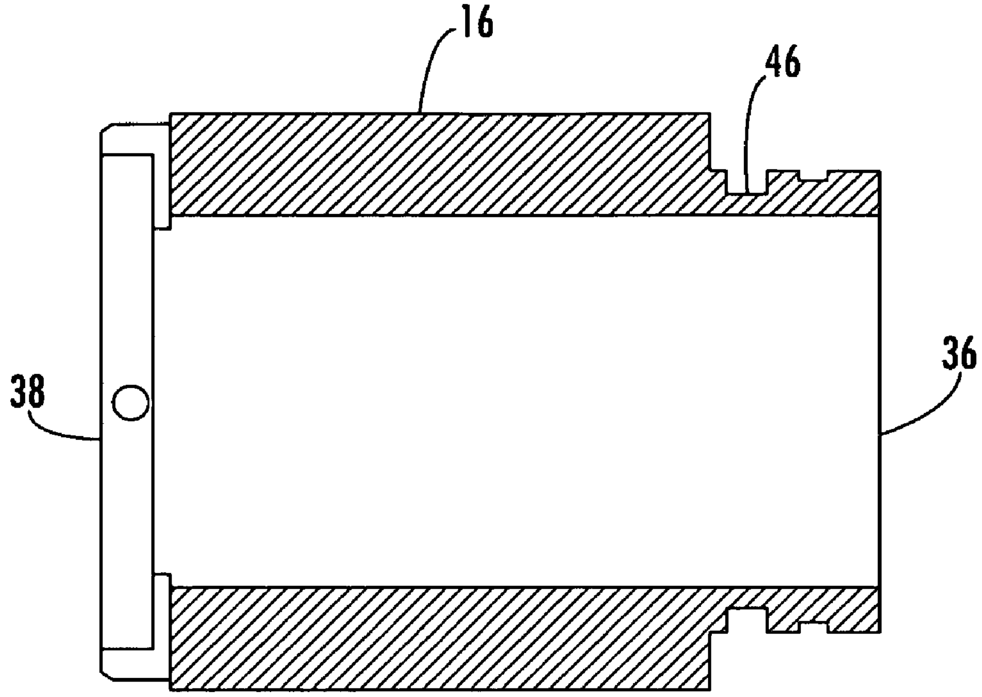
FIGS. 6*a-b* are views of the quick release cap of the shielded radioactive medical container according to a preferred embodiment of the invention.
Figure 6B:
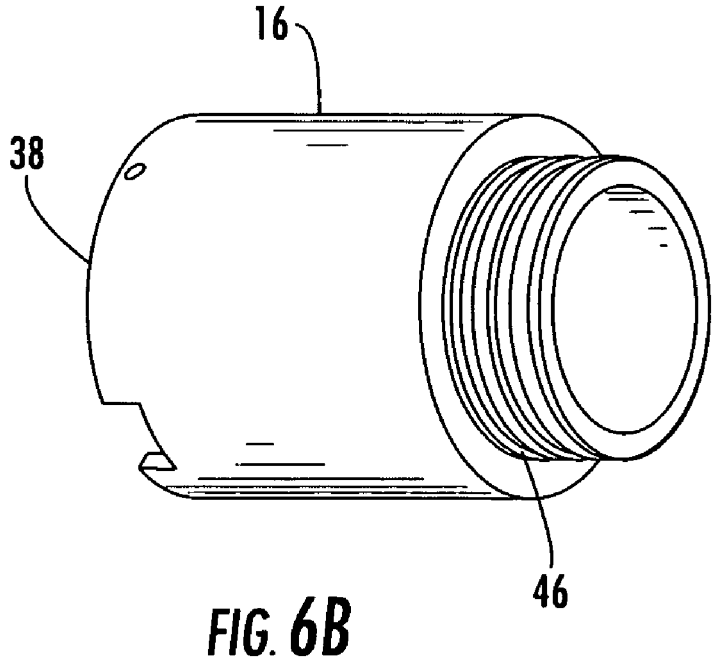

Referring now to FIG. 2, there is shown an exploded view of a preferred embodiment of the shielded radioactive medical container 10. As shown in FIGS. 5A and 5B, the housing 12 is tubular with an open end and a closed end. The tubular housing 12 is preferably cylindrical, but in alternate embodiments may be a square tube, rectangular tube or any other shaped tube.

Lower shield 20 is located in the interior of the housing 12 and preferably has a tubular configuration to fit snugly within the housing 12. The lower shield 20 has a cavity 34 with an opening which allows a radioactive object to be placed within the cavity 34 from the open end of the housing 12. The cavity 34 is preferably sized to allow a syringe to fit therein. The lower shield 20 may be made of any material which is suitable for shielding radiation, and is preferably lead or tungsten.

The open end of the housing 12 is configured so that the proximate end 36 of the quick release cap 16 fits inside of the housing 12. When the quick release cap 16 is secured onto the housing 12, the proximate end 36 of the cap 16 is located within the open end of the housing 12. An upper shield 22 is located within the interior of the quick release cap 16 and acts as a radioactive shield which closes off the cavity 34 in the lower shield 20 when the cap 16 is secured on the housing 12. The upper shield is preferably cylindrical in shape and made of the same material as the lower shield 20.

Figure 3:
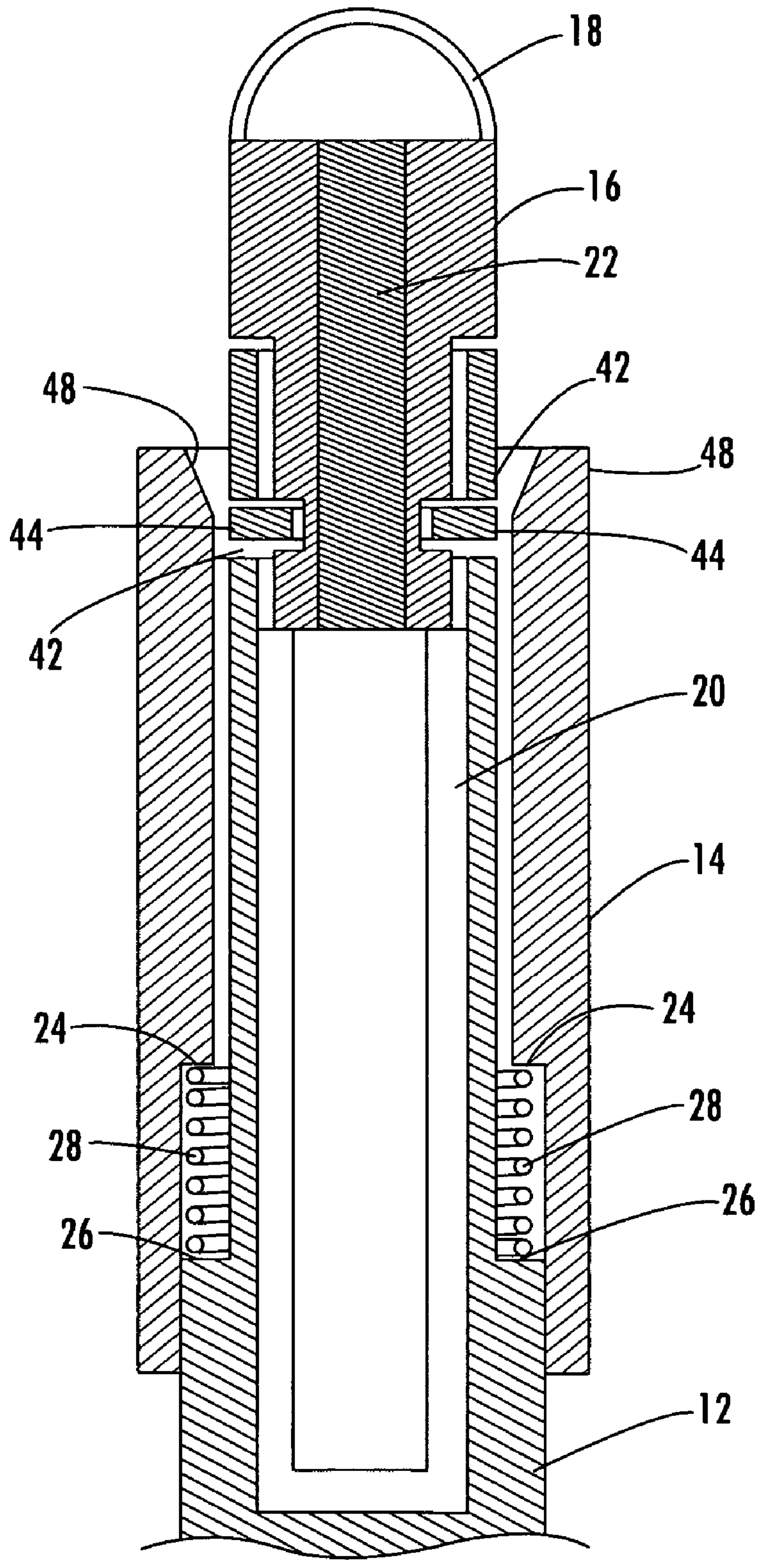
FIG. 3 is a cross sectional view of the shielded radioactive medical container according to a preferred embodiment of the invention.
Figure 4:
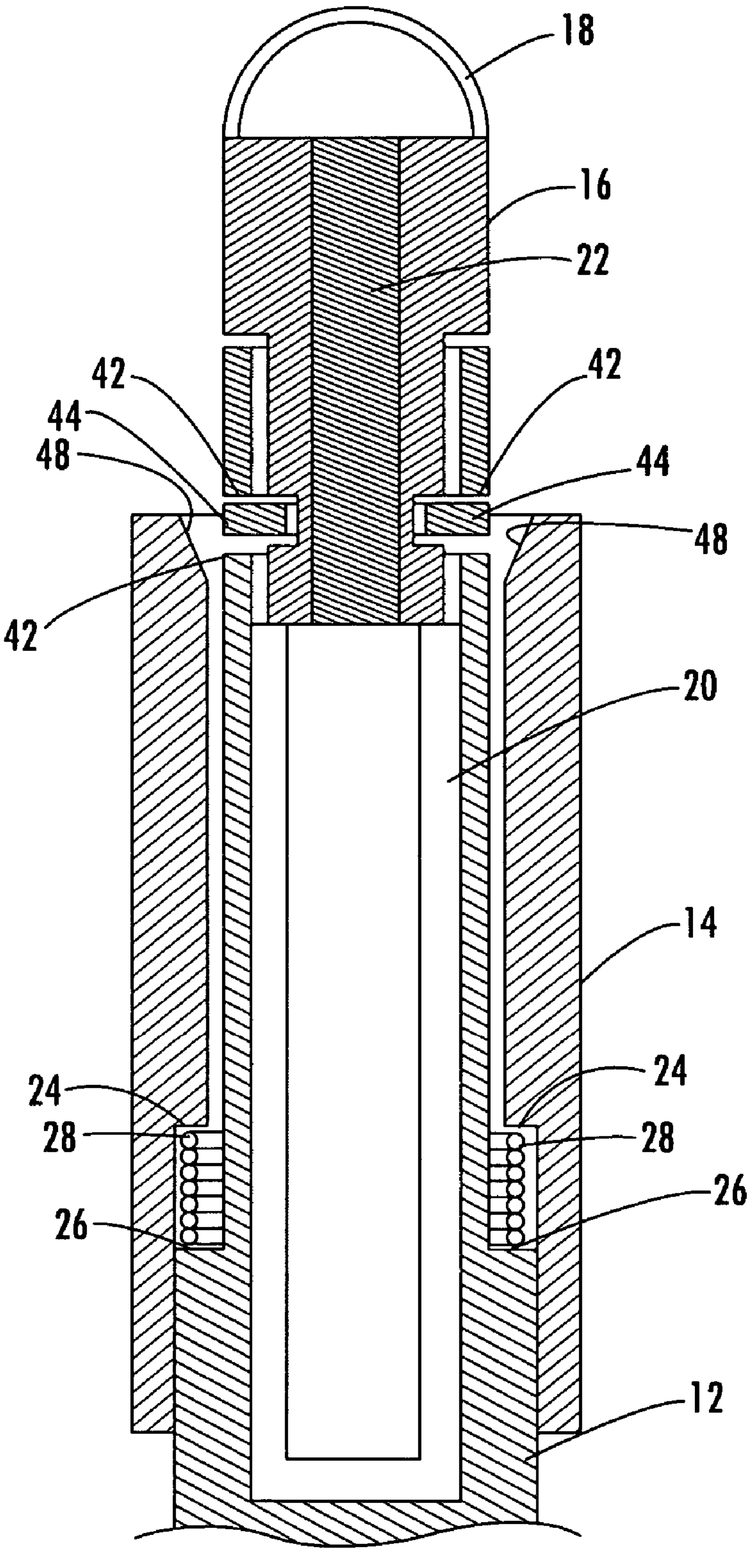
FIG. 4 is another cross sectional view of the shielded radioactive medical container according to a preferred embodiment of the invention.

Collar 14 is located on the exterior of the housing 10. Referring now to FIGS. 3 and 4, the exterior of the housing 12 has a shoulder 26 located proximate the open end. A spring 28 rests on the housing shoulder 26. The collar spring 28 biases the collar 14 towards the open end of the housing 12 by placing a biasing force on a shoulder 24 located on the interior of the collar 14.

The collar 14 operates a quick release mechanism which is preferably a pin and receiver mechanism 40. A plurality of bores 42 are located on the housing 12 proximate the open end of the housing 12. A pin mechanism 44 is located within each the plurality of bores 42. The plurality of pins 44 are formed to fit within a receiver on the quick release cap 16. In a preferred embodiment, the receiver is a groove 46 located on the proximate end 36 of the quick release cap 16. In alternate embodiments the receiver may be bores located in the cap 16 or other devices configured to receive pins.

Pin springs located within the pins 44 bias the plurality of pins 44 away from the groove 46. However, as shown in FIG. 3, when the collar 14 is in the up position, as normally biased by the collar spring 28, the inclined engagement surfaces 48 on the collar 14 engage the plurality of pins 44 and press them into the groove 46 on the quick release cap 16. Thereby, the pin and receiver mechanism 40 secures the quick release cap 16 onto the housing 12 and allows the container 10 to be transported with minimal radiation emitted from the container 10.

When medical personnel desire to remove a radioactive object from the container 10, the process can be done quickly using the quick release mechanism of the present invention. A user pushes the collar 14 into a down position, as shown in FIG. 4. When the collar 14 is in the down position, the pins 44 are biased away from the groove 46 on the quick release cap 16 by the pin springs. The quick release cap 16 may then be quickly and easily removed from the housing 12.

Alternatively, the quick release mechanism may consist of balls movably located in the plurality of bores 42. When the collar 14 is in the up position, the inclined engagement surfaces force the balls into the groove 46 on the quick release cap 16, holding the cap in place. When the collar 14 is in the down position, the movable balls are no longer forced into the groove 46 and the quick release cap 16 may be removed.

Figure 7B:
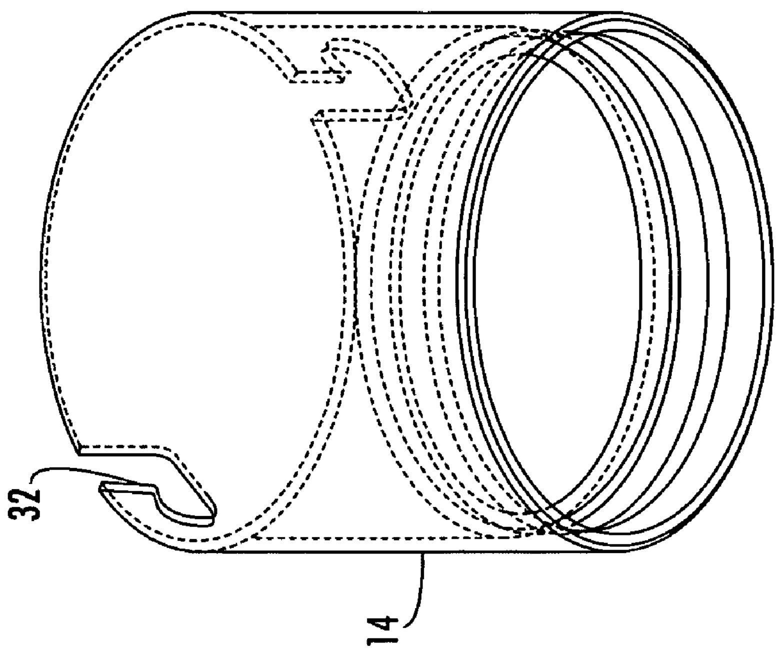
FIGS. 7*a-b* are views of the collar of the shielded radioactive medical container according to a preferred embodiment of the invention.
Figure 7A:
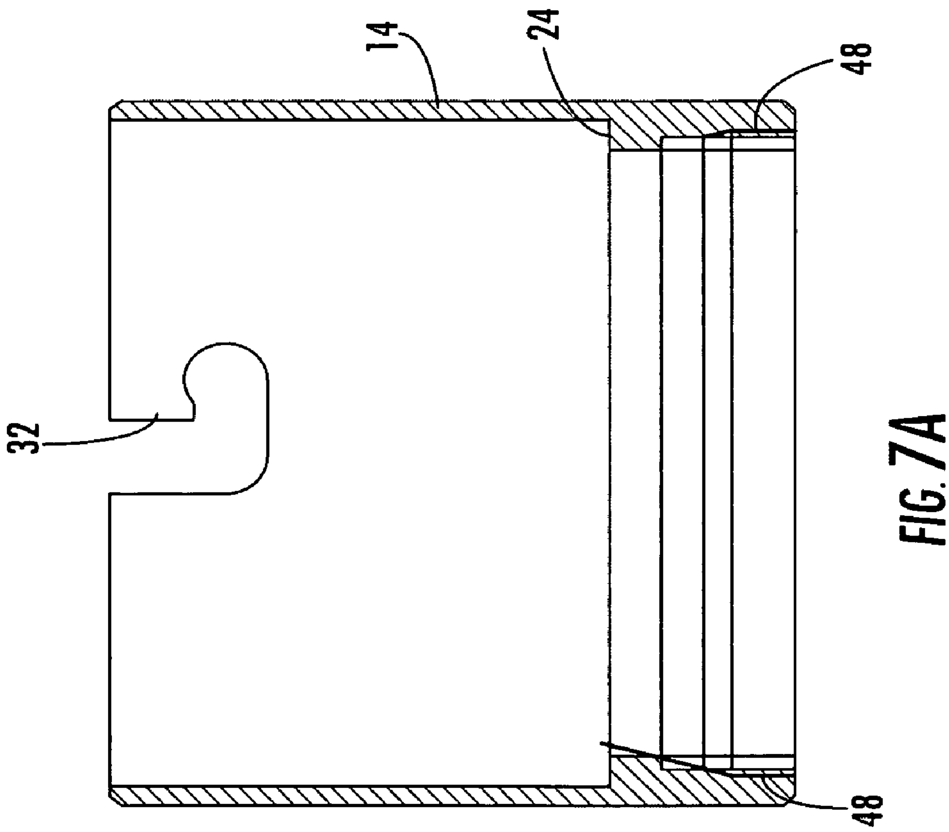

Referring to FIGS. 7A and 7B, a right angled slot 32 is located on the collar 14 which is configured to mate with a protrusion 30 on the housing 12. When a user places the collar 14 in the down position, they may slide the right angled slot 32 onto the protrusion 30 and twist the collar 14, thereby securing the collar 14 in the down position. This allows the user to more quickly and dexterously perform tasks by removing the need for using one hand to keep the collar 14 in the down position. Further, the quick release cap 16 may be quickly replaced back onto the housing 12 when the collar 14 is secured in the down position.

In a preferred embodiment, the handle 18, is a bail handle located on the distal end 38 of the quick release cap 16 and is pivotable on the end of the quick release cap 16. In other words, the handle 18 may be pivoted to a position perpendicular to the distal end 38 of the quick release cap 16, so that the container 10 may be easily carried by medical personnel and the quick release cap 16 may be easily removed. The handle 18 may be pivoted to a position parallel to the distal end 38 of the quick release cap 16, so that the container 10 may be more easily stored. In one embodiment of the invention, the handle 18 may lay in a recess in the distal end 38 of the quick release cap 16.

Figure 8B:
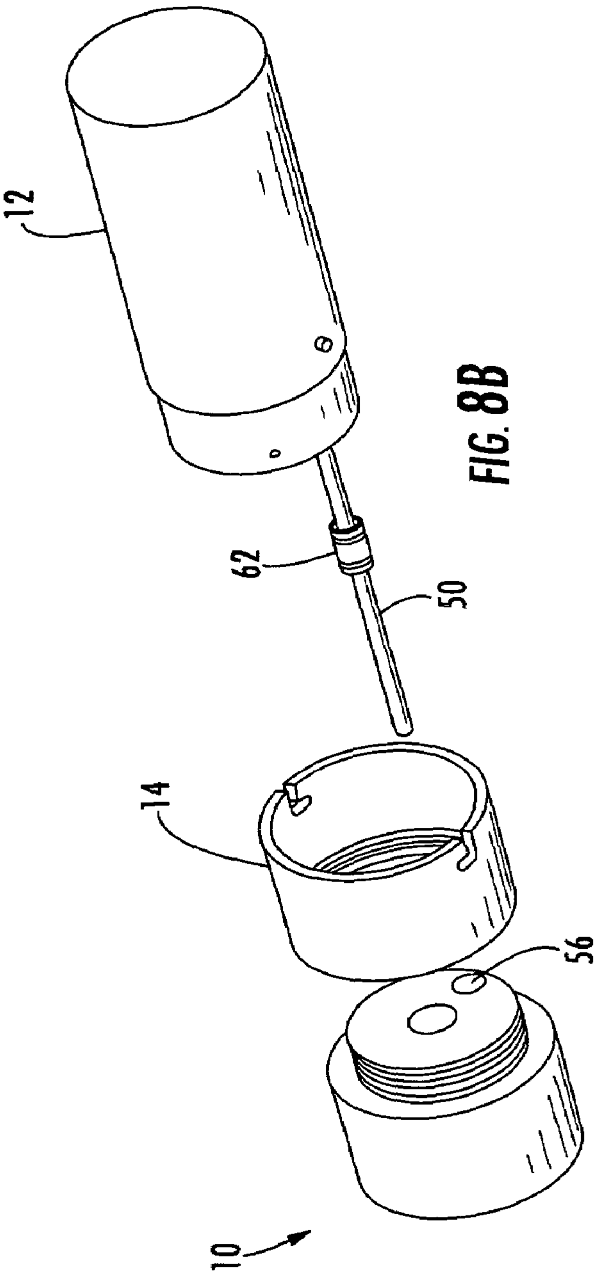
FIG. 8*b* is an exploded view of the shielded radioactive medical container according to an alternate embodiment of the invention.
Figure 8A:
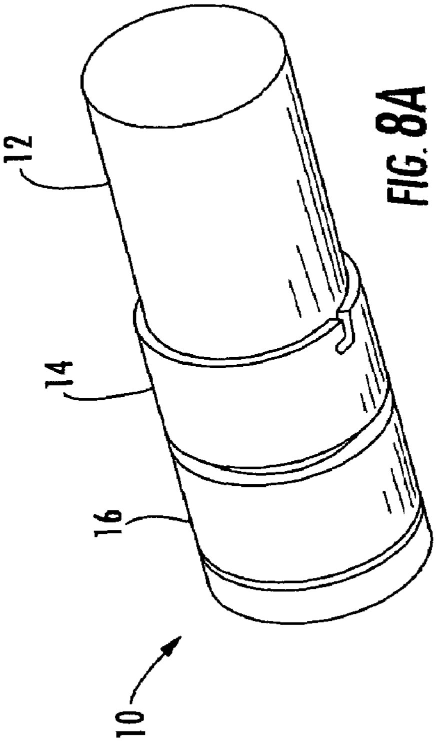
FIG. 8*a* is a view of the shielded radioactive medical container according to an alternate embodiment of the invention.
Figure 9B:
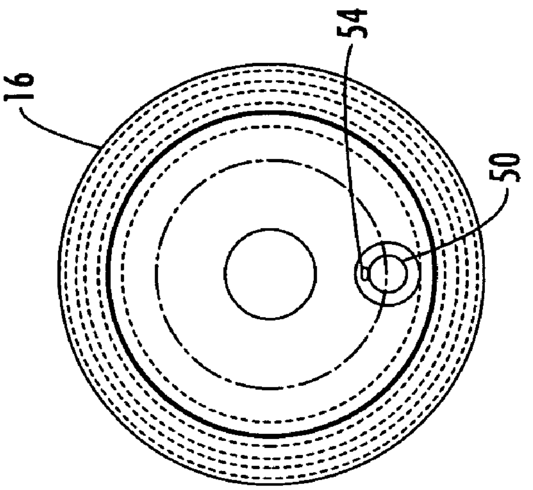
FIGS. 9*a-b* are views of the quick release cap of the shielded radioactive medical container according to an alternate embodiment of the invention.
Figure 9A:
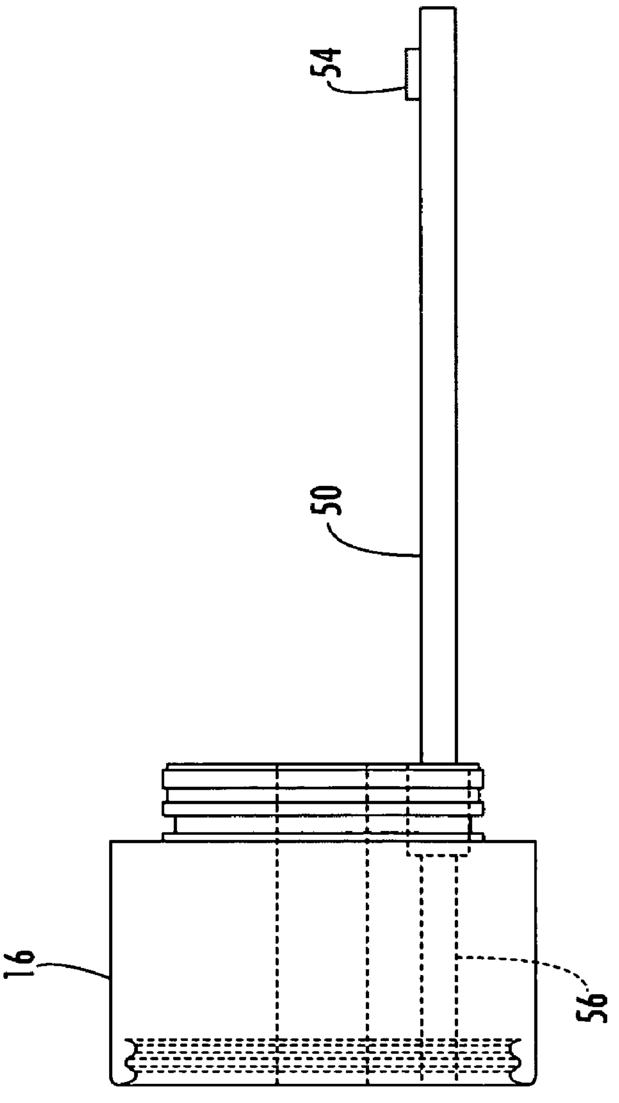

An alternate embodiment of the invention, as shown in FIGS. 8*a* and 8*b*, utilizes a keyed rail 50 located in a slotted cavity 52 to assist in properly removing the quick release cap 16 from the housing, without contacting, and possibly damaging a radioactive object within the container 10. As shown in FIGS. 9*a-b*, a keyed rail 50 is located and securely attached in a rail cavity 56 in the quick release cap 16. The keyed rail 50 extends outwardly from the proximate end of the cap 16 and includes a key 54 proximate the end of the rail opposite the cap 16.

Figure 10C:
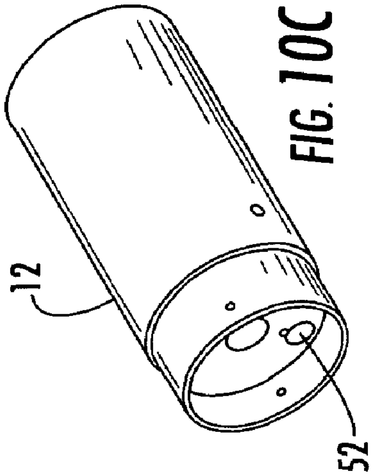
FIGS. 10*a-c* are views of the housing of the shielded radioactive medical container according to an alternate embodiment of the invention.
Figure 10B:
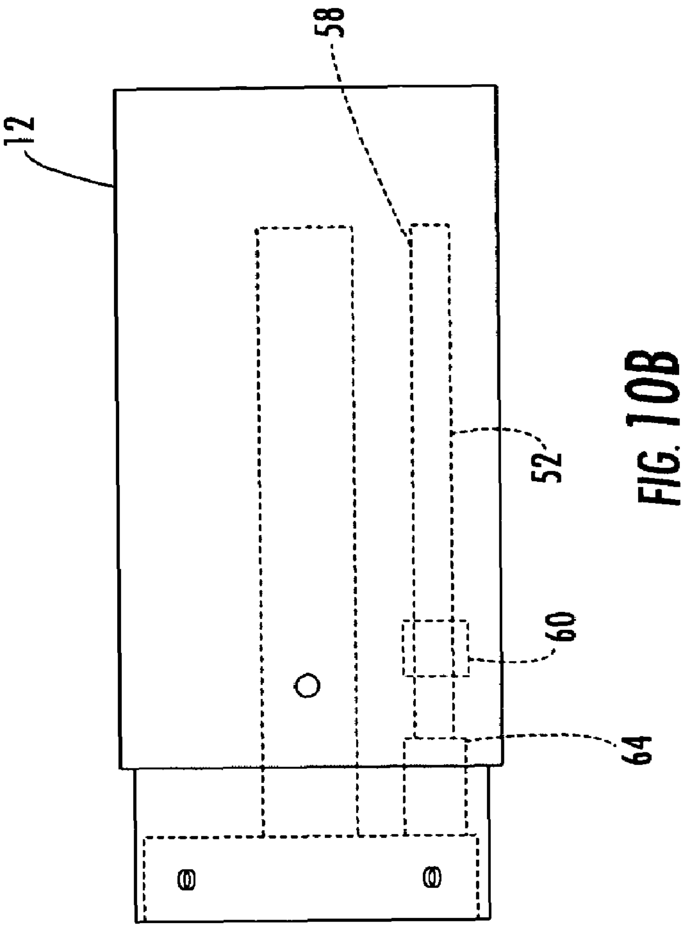
Figure 10A:
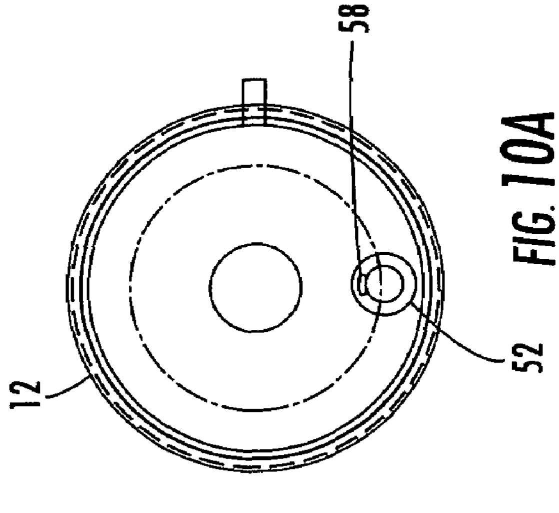

As shown in FIGS. 10*a-c*, the housing includes a slotted cavity 52 having a slot 58 extending along its length. The cavity 52 has an opening 64 in the open end of the housing 12. Guide bearing 62 is located in the opening 64. The slotted cavity includes a cutout 60 proximate the open end of the housing. The keyed rail 50 on the quick release cap 16 is slidably located on the guide bearing 62 in the slotted cavity 52. The key 54 mates with the slot 58 in the cavity 52, which allows the cap 16 to be moved away form the housing 12, while not allowing the cap 16 to rotate about the rail 50. This prevents the cap from contacting the radioactive object located in the interior. When the cap has move outwardly a sufficient distance from the cap and radioactive object, the key 54 is located in the cutout 60, allowing the cap 16 to be rotated, so that the radioactive object may be removed.

Multiple slots may be located in the cavity, allowing the cap 16 to be lowered onto the housing in a position where the cap will not contact the radioactive object. In other embodiments, the rail 50 may be slotted, with a key located in the cavity 52 or the shielded container may utilize other slot/key mechanisms. Further, the rail and cavity may be external to the housing 12, contained within a separate independent housing attached to the shielded container.

Figure 11B:
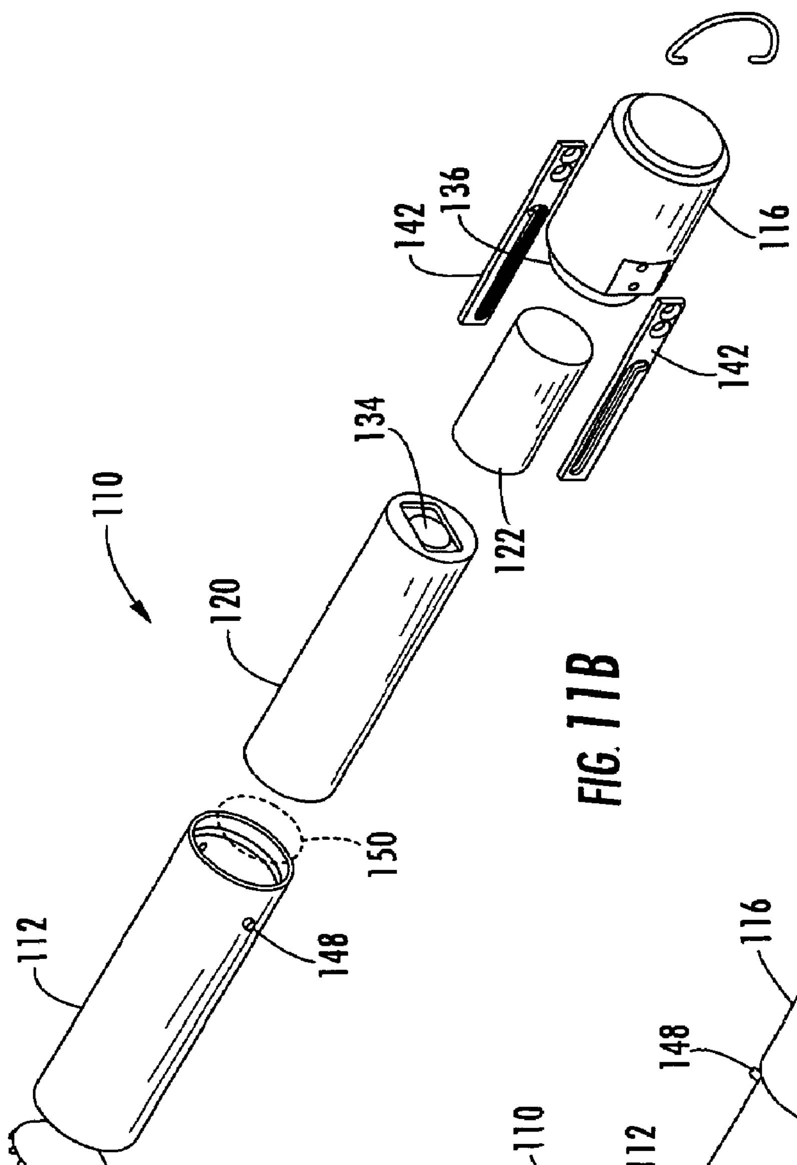
FIG. 11*b* is an exploded view of the shielded radioactive medical container according to a second alternate embodiment of the invention.
Figure 11A:
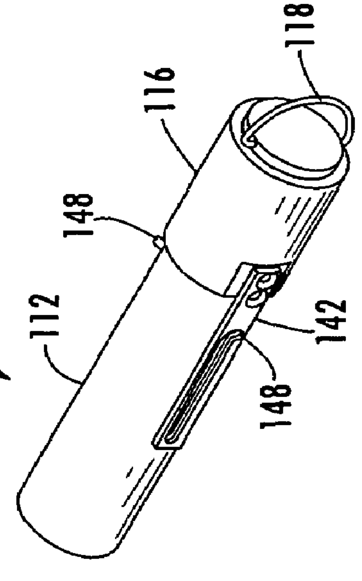
FIG. 11*a* is a view of the shielded radioactive medical container according to a second alternate embodiment of the invention.
Figure 12A:
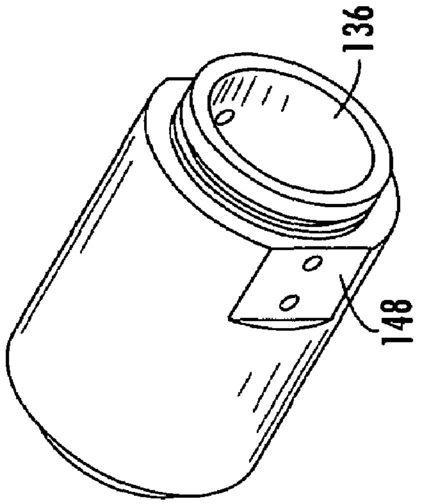
FIGS. 12*a-d* are views of the quick release cap of the shielded radioactive medical container according to a second alternate embodiment of the invention.
Figure 12B:
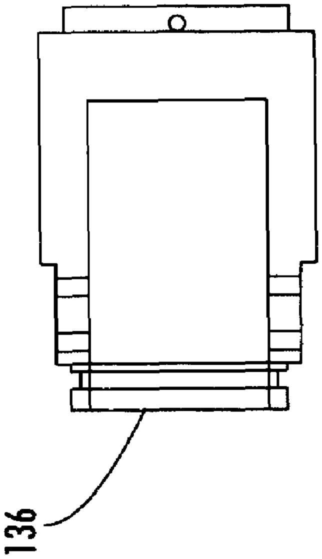
Figure 12C:
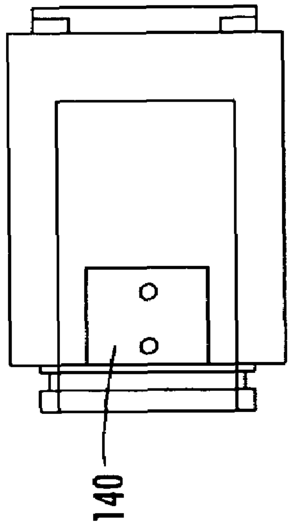
Figure 12D:
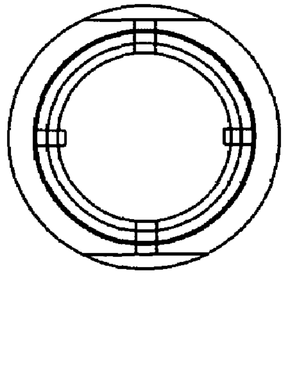

Another alternate embodiment of the present invention is shown in FIGS. 11*a* and 11*b* and utilizes a flip top mechanism as the quick release mechanism. The shielded container 110 of this embodiment includes a housing 112, a quick release cap 116, and a handle 118.

Referring now to FIG. 11*b*, there is shown an exploded view of this alternate of the shielded radioactive medical container 110. The housing is preferably tubular, with a closed end and an open end. The tubular housing 112 is preferably cylindrical, but in alternate embodiments may be a square tube, rectangular tube or any other shaped tube.

Lower shield 120 is located in the interior of the housing 112 and preferably has a tubular configuration to fit snugly within the housing 12. The lower shield 120 has a cavity 134 with an opening which allows a radioactive object to be placed within the cavity 134 from the open end of the housing 112. The cavity 134 is preferably sized to allow a syringe to fit therein. The lower shield 120 may be made of any material which is suitable for shielding radiation, and is preferably lead or tungsten.

The open end of the housing 112 is configured so that the proximate end 136 of the quick release cap 116 fits inside of the housing 112. When the quick release cap 116 is secured onto the housing 112, the proximate end 136 of the cap 116 is located within the open end of the housing 112. An upper shield 122 is located within the interior of the quick release cap 116 and acts as a radioactive shield which closes off the cavity 134 in the lower shield 120 when the cap 116 is secured on the housing 112. The upper shield 122 is preferably cylindrical in shape and made of the same material as the lower shield 120.

Figure 13A:
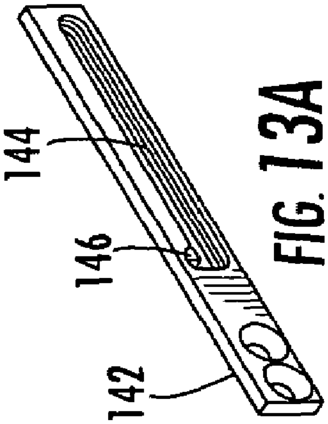
FIGS. 13*a-c* are views of the slotted flip top arm of the shielded radioactive medical container according to a second alternate embodiment of the invention.
Figure 13C:
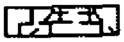
Figure 13B:
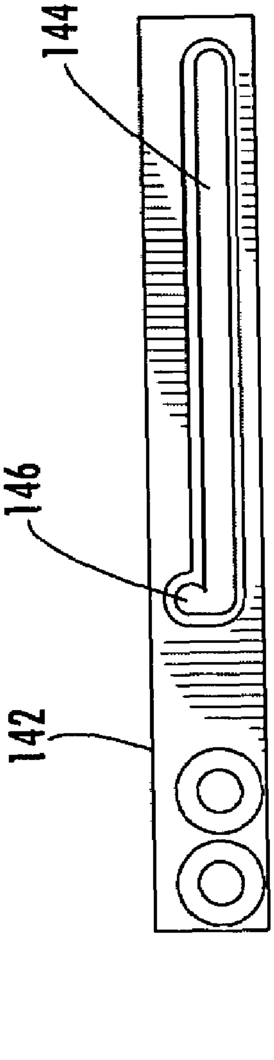
Figure 14B:
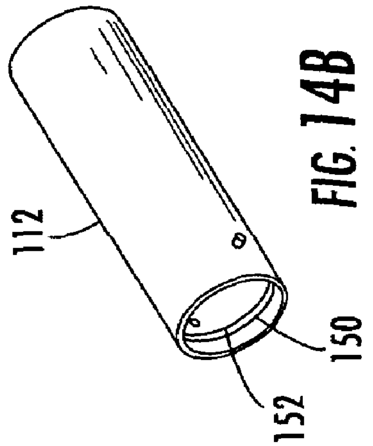
FIGS. 14*a-c* are views of the housing of the shielded radioactive medical container according to a second alternate embodiment of the invention.
Figure 14A:
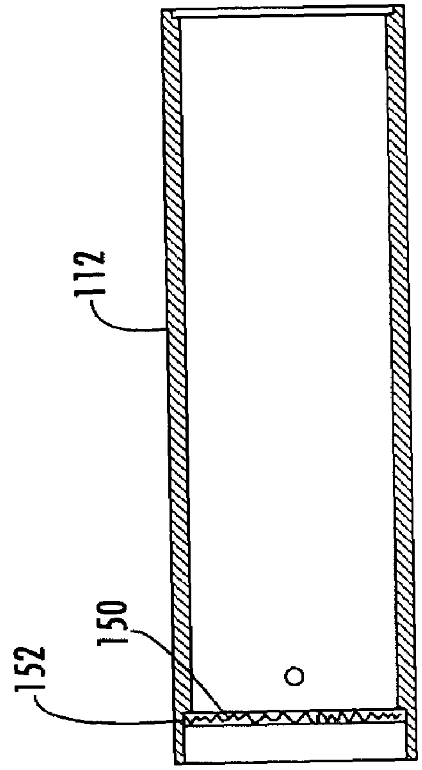
Figure 14C:
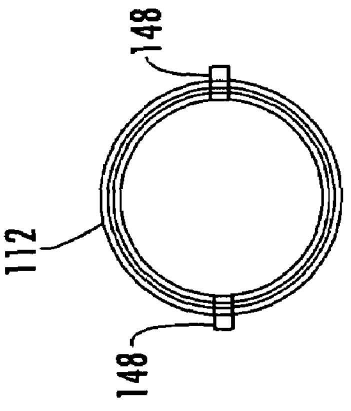

As shown in FIGS. 12*a-d*, the quick release cap 116 has a plurality of level surfaces 140, where a flip top arm 142 (shown in FIGS. 13*a-c*) is attached. The flip top arm 142 has a slot 144 having a right angled portion 146 on the end of the slot 144 closest to the quick release cap 116. Dowels 148 located in bores located proximate the open end of the tubular housing 112 are slidably located in the slots 144 in the flip top arms 142. As shown in FIGS. 14*a-c*, a disc spring 150 is located in the interior groove 152 in the open end of the tubular housing 112 to provide a biasing force against the quick release cap 116 when the cap is secured on the housing.

The flip top arms 142, dowels 148, and disc wave spring 150 act as a quick release mechanism for this alternate embodiment of the invention. When a user desires to close and secure the container 110, the quick release cap is slid into position onto the open end of the tubular housing 112. The quick release cap 116 is then twisted, so that the dowels 148 slide into the right angled portion 146 of the arm's slots 144. The biasing force created by the disc wave spring 150 holds the dowels 148 in position in the right angled portion 146.

To remove a radioactive object from the container 110, the quick release cap 116 is twisted so that the dowels 148 are no longer in the right angled portion 146 of the slots 144. The quick release cap 116 is then slid up and off of the tubular housing. The quick release cap 116 may then be pivoted to a position allowing the radioactive object to be removed. The quick release cap 116 is thereby easily and quickly removed from the tubular container, allowing improved access to the radioactive object.

Figures 15A, 15B:
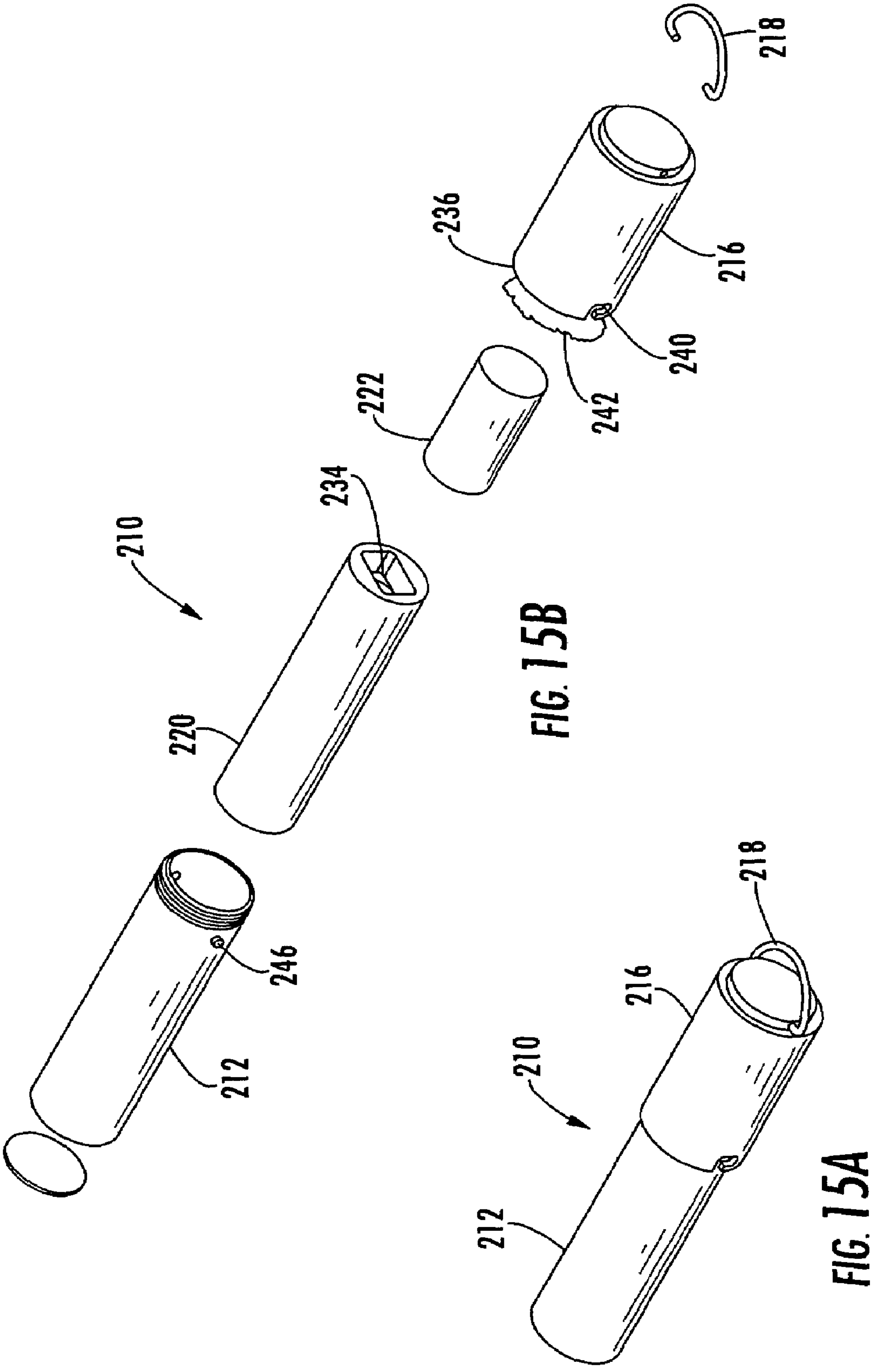
FIG. 15*a* is a view of the shielded radioactive medical container according to a third alternate embodiment of the invention.
FIG. 15*b* is an exploded view of the shielded radioactive medical container according to a third alternate embodiment of the invention.
Figure 16A:
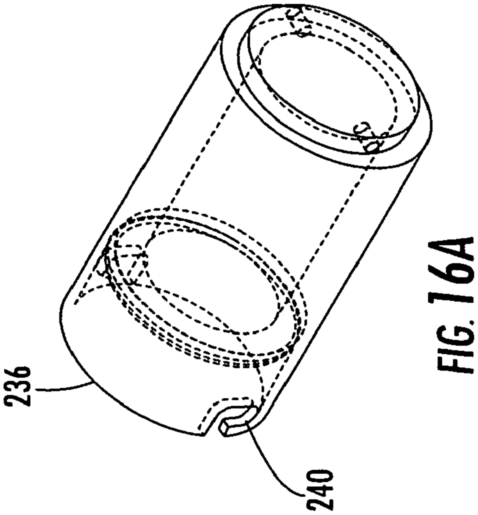
FIGS. 16*a-d* are views of the quick release cap of the shielded radioactive medical container according to a third alternate embodiment of the invention.
Figure 16D:
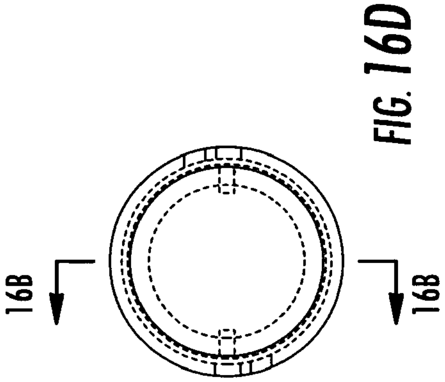
Figure 16B:
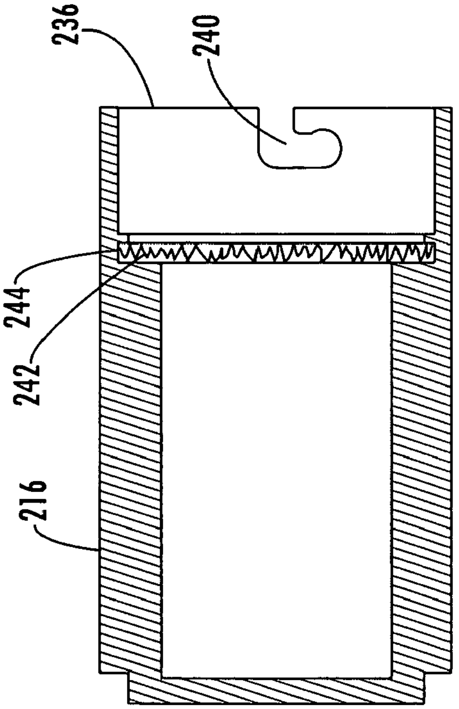
Figure 16C:
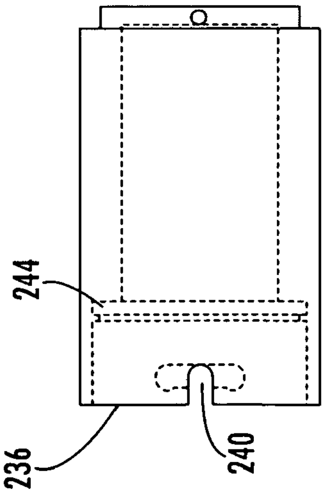

Another alternate embodiment of the present invention is shown in FIGS. 15*a* and 15*b* and utilizes a twist top mechanism as the quick release mechanism. The shielded container 210 of this embodiment includes a housing 212, a quick release cap 216, and a handle 218.

Referring now to FIG. 15*b*, there is shown an exploded view of this alternate of the shielded radioactive medical container 210. The housing is preferably tubular, with a closed end and an open end. The tubular housing 212 is preferably cylindrical, but in alternate embodiments may be a square tube, rectangular tube or any other shaped tube.

Lower shield 220 is located in the interior of the housing 212 and preferably has a tubular configuration to fit snugly within the housing 212. The lower shield 220 has a cavity 234 with an opening which allows a radioactive object to be placed within the cavity 234 from the open end of the housing 212. The cavity 234 is preferably sized to allow a syringe to fit therein. The lower shield 220 may be made of any material which is suitable for shielding radiation, and is preferably lead or tungsten.

The open end of the housing 212 is configured so that the proximate end 236 of the quick release cap 216 fits over the exterior of the housing 212. When the quick release cap 216 is secured onto the housing 212, the proximate end 236 of the cap 216 is located over the open end of the housing 212. An upper shield 222 is located within the interior of the quick release cap 216 and acts as a radioactive shield which closes off the cavity 234 in the lower shield 220 when the cap 216 is secured on the housing 212. The upper shield 222 is preferably cylindrical in shape and made of the same material as the lower shield 220.

Figure 17B:
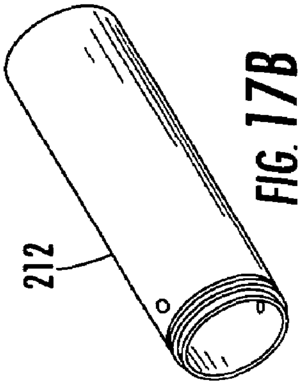
FIGS. 17*a-c* are views of housing of the shielded radioactive medical container according to a third alternate embodiment of the invention FIGS. 18-20 skipped.
Figure 17A:
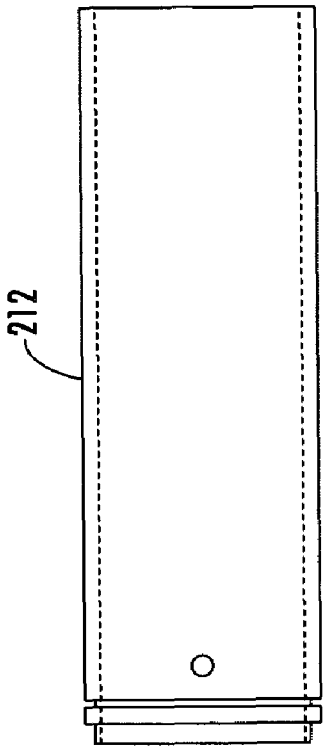
Figure 17C:
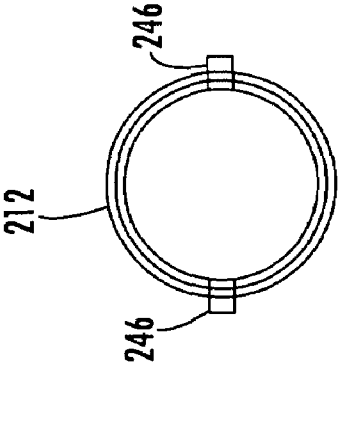

As shown in FIGS. 16*a-d*, a plurality of right-angled slots 240 are located in the proximate end 236 of the quick release cap 216. A disc wave spring 242 is located in the interior groove 244 in the quick release cap and provides a biasing force against the tubular housing 212 when the quick release cap is secured on the housing. As shown in FIGS. 17*a-c*, dowels 246 are located in bores proximate the open end in the tubular body. These dowels 246 are configured to fit within the right angle slots 240 on the quick release cap. The dowels, slots, and spring form the quick release mechanism of this alternate embodiment of the invention.

When a user desires to close and secure the container 210, the quick release cap is placed into position on the open end of the tubular housing 212. The quick release cap 216 is lowered and then twisted, so that the dowels 246 on the tubular housing 212 slide into the right angled slots 240. The biasing force created by the disc wave spring 242 holds the dowels 246 in position in the right angled slots 240.

To remove a radioactive object from the container 210, the quick release cap 216 is twisted and lifted so that the dowels 246 are no longer positioned in the right angled slots 240 on the quick release cap 216. The quick release cap 216 is thereby easily and quickly removed from the tubular container, allowing improved access to the radioactive object.

FIGS. 21-29 illustrated an automated version of the safety shields (medical containers) described above. The automated safety shields are incorporated into a computer system that is integrated into other computer systems, such as computer systems found in pharmacies, hospitals, clinics and doctor's offices. Thus, the automated safety shields enable efficient handling of both the radioactive pharmaceutical and the related information necessary to use the pharmaceutical.

Automated Safety Data Shields

Over 13,000,000 unit doses of radioactive pharmaceuticals are administered in the US each year for the management of a variety of diseases that employ nuclear medicine techniques in their diagnosis, staging, and/or treatment. The inherent nuclear properties of these materials result in their on-going loss due to radioactive decay processes that by their very nature provide the necessary radiations that enable their diagnostic and/or therapeutic applications in nuclear medicine. These same nuclear properties, however, require that certain precautions be strictly followed in the handling and use of these unique pharmaceuticals in order to protect personnel and staff from excessive exposures to radiation.

The current shielding and packaging systems and products used to transport and handle radioactive pharmaceuticals are flawed in two primary respects: a) shielding components are not integrated, thus requiring personnel to unshield radioactive sources and place it into individual and different devices for the dispensing and packaging, transportation, patient delivery, and administration of the desired radiopharmaceutical, and b) though considerable information regarding the radiopharmaceutical are processed and recorded using relatively sophisticated data management programs, much of critical data associated with the radiopharmaceutical identity and its disposition are still tracked manually and in hard-copy form, with key information entered at some point following the administration of the drug. In this manner, timely information relating to the amount of radioactivity contained in a unit dose at any given moment must be manually calculated relative to the half-life of the radioactive material, and the time of actual administration (and quantity administered) are necessarily recorded first by hand, and then later entered into the patient's data file. Both these actions are subject to human errors, and inaccuracies associated with manual processing of data and its notation.

The Current Situation—Patient and Radiopharmaceutical Information and Channels/Points Process at Hospital—Initiation of Patient Dose Data The hospital nuclear medicine department typically initiates the process leading to the dispensing of a unit-dose, patient-specific radiopharmaceutical from an off-site dispensing radiopharmacy by providing the disposing pharmacist with the following specific information as may be required for the daily requirements of their nuclear medicine patients:

a. Patient Identity
b. Radiopharmaceutical requirements
  Name of radiopharmaceutical
  Amount of radioactivity required
  Prescribing physician
  Time of desired administration (i.e., 'calibration' time)

Hospital personnel often verbally transfer information to dispensing radiopharmacy, though greater use of electronic transmission of hospital data to dispensing radiopharmacy is occurring.

Essential equipment used in the process of 'filling' prescriptions for radiopharmaceuticals includes: Radionuclide dose calibrator(s) (for measuring the amount of radiopharmaceuticals), sturdy transport cases with syringe transport shields (shields for 'over-the-road' transportation of syringes from the dispensing pharmacy to the hospital), syringe carrier shields (for handling syringes containing radioactive to patient administration areas), syringe injection shields—used to safely contain syringes during patient administration, a computerized radiopharmacy information system (RxIS) (usually provided by dispensing radiopharmacy to hospitals for the purpose of tracking and processing salient information about the radiopharmaceutical, including its receipt and disposition).

Dispensing Pharmacy—Filling Prescription for Nuclear Medicine Patients

At the dispensing pharmacy, current Rx Information Systems (RxIS) serve as dispensing programs that calculate the up-to-date amounts of the radiopharmaceuticals, manage quantities of radiopharmaceutical in inventory, matches hospitals' patients' requirements with product availability, creates hard copy labels of individual prescriptions and records of aggregate prescription data, prepares shipping manifest with bar coding, and creates billing records for hospital customers. Upon entering hospitals' patients' information and dose needs, the RxIS determines:

a. Radiopharmaceutical to be dispensed
b. Radiopharmaceutical identity (lot number, compounding data, etc.)
c. Amount and volume of desired radiopharmaceutical at intended time of administration Dispensing pharmacist removes (or 'draws') the specified volume of the desired radiopharmaceutical into a unit dose syringe, then-using a radionuclide dose calibrator-he/she assays (i.e., measures) the amount of radioactivity in syringe at that moment, and determines the future value of the dose at the intended time of administration as the amount of radioactivity remaining beyond the appropriate decay interval. This value is obtained either by calculations performed by the dispensing radiopharmacy RxIS program, or by an operator-assisted program on the radionuclide dose calibrator. In all situations, the dose calibrator discriminates only the amount of radionuclide present, a process that is based upon specific nuclear properties of the radionuclide. The dose calibrator does not identify the specific radiochemical form of this radioactive element. In medical practice, it is the complex of the radionuclide in the desired radiochemical form that constitutes the radiopharmaceutical identity that affords the properties of biological distribution.

With the proper amount of desired radiopharmaceutical contained in the unit dose syringe, a hard-copy prescription label is printed that generates a record of:

a. Patient Identity
b. Hospital Identity
c. Radiopharmaceutical Identity
  Name of Radionuclide
  Amount contained at intended time of administration
  Intended time of administration, date
  Volume contained
  Prescription number (generated by pharmacy MIS)
d. Radiopharmaceutical expiration time The dispensing radiopharmacy places each syringe into a transport shield (usually manufactured of lead or tungsten), and labels the exterior with a hard copy of the prescription data. The syringe transport shield is packaged in a transport container (that holds multiple syringe transport shields) to be delivered to the customer hospital by courier personnel.

Hospital—Receipt of Prescribed Radiopharmaceuticals, Administration, Recordkeeping, Return Presently, at the hospital, personnel check in each patient dose, usually by first swiping the corresponding bar code that reconciles patient dose information into the hospital's RxIS data management system. The transport shield is usually opened at this point, and the syringe is transferred to the syringe carrier shield that is used to safely contain the radioactive syringe to the patient's side. Once at the patient side, the syringe is removed once more and placed into a smaller injection shield that is used to shield the person performing the patient administration. The staff member records the time of patient administration (a critical factor that affects the timing of the patient's scan to be performed later), and—at some later time—manually enters this information into the patient's nuclear medicine database, along with the identity of the person performing the actual administration. The spent syringe is removed from the injection shield, transferred back to the in-house syringe carrier shield. Eventually, the syringe is re-packaged into the original transport shield that is finally returned to the dispensing radiopharmacy. Each syringe transfer containing the radioactive dose from one container to another or from one container to a shield and back again results in additional radiation exposure to hospital staff.

The ORTG Radiopharmaceutical Dose Containment System

The ORTG Dose Containment System is an integrated line of products which encompasses the spectrum of safety shielding and radiopharmaceutical information from the initial dispensing of the product through its transportation from the pharmacy to the user hospital, its disposition, and the subsequent return of the spent syringe to the dispensing nuclear pharmacy. The system products utilize superior component design and fabrication, that couples with new technology to maintain up-to-date information on the radiopharmaceutical dose, all in a convenient package concept that maintains personnel radiation exposures to their lowest achievable levels.

The products consist of the following:

a. SafetyDATA Shields (SDS)

b. Shipping/transport cases for SDS units c. Wireless interface between SDS and Radionuclide Dose Calibrator or MIS SafetyDATA Shields Referring to FIGS. 21-23, the SafetyDATA Shield is a unit dose syringe transport shield that safely contains unit doses of radioactive pharmaceuticals from the point of dispensing entirely to the patient's side and administration.

The SafetyDATA Shield (SDS) is designed with two novel features that favorably address user convenience and lower personnel exposures while allowing users to determine, reconcile, and document certain critical patient-specific data by electronic means in an automated fashion. The SDS's data module—a proprietary microprocessor with an LCD coupled to wireless [in this embodiment, an InfraRed (IR)] communication component—is initially loaded by the dispensing pharmacist with the relevant dose-specific digital information that is subsequently displayed on the SDS's battery-powered LCD screen located on the face of the top of the unit. The dose-specific information uploaded by the pharmacist includes, but is not limited to, the following information about the radiopharmaceutical contained within the SDS:

Patient identity,

Prescription number,

Prescription

Name of radionuclide and chemical form,

Amount of dispensed radioactivity, and

Hospital identity.

Figure 22:
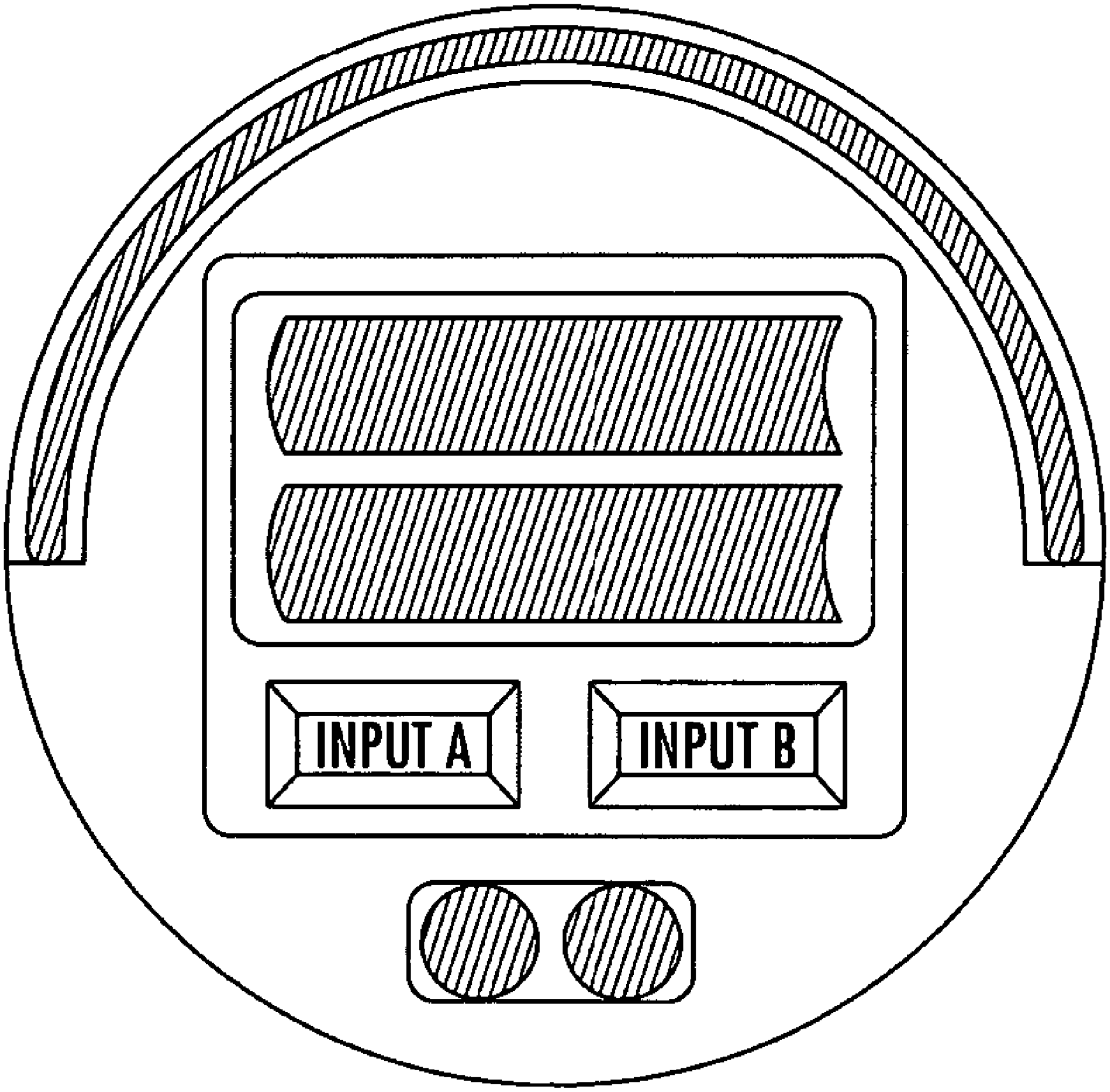
FIG. 22 is a top view of the cap for the safety shield showing the electronic display.
Figure 25:
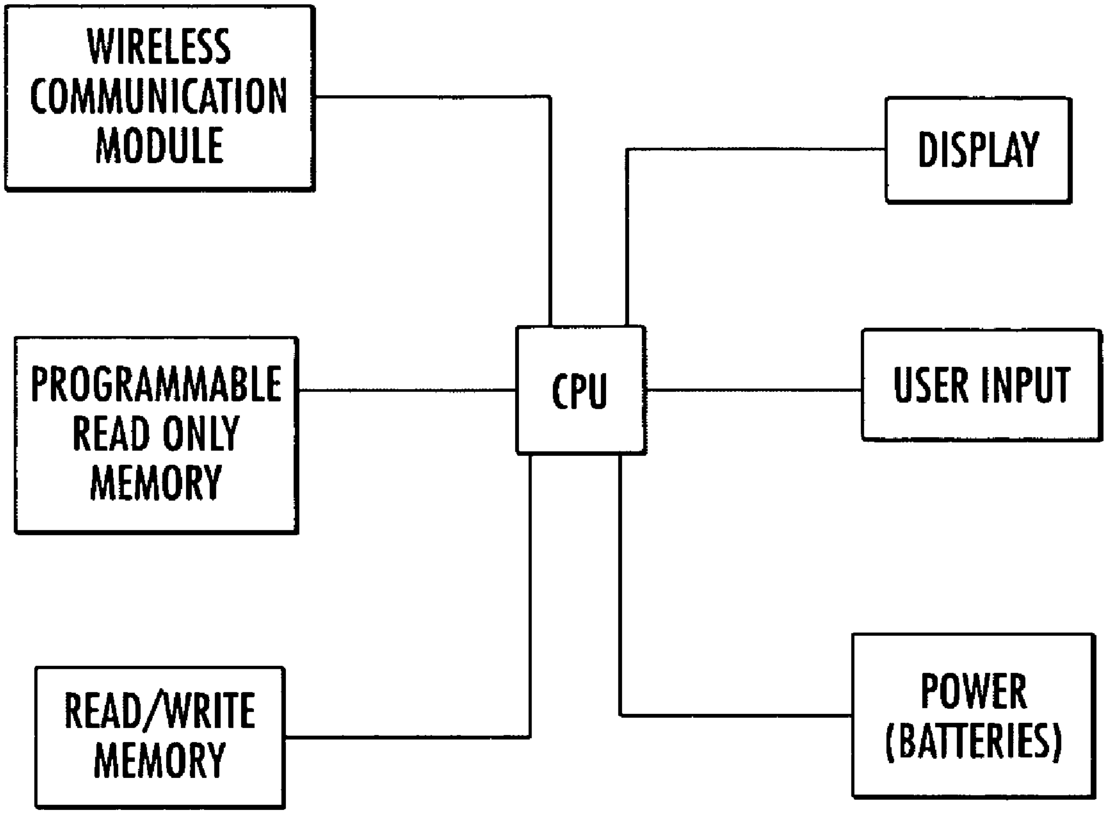
FIG. 25 is a block diagram of the electronics contained within the cap of the shield.

Referring to FIG. 25, a block diagram of the electronic data module is shown. It includes a central processing unit (CPU) that is preferably a microprocessor but could also be a special purpose chip, such as an ASIC. The CPU is connected to a user input which is preferably buttons as shown in FIG. 22. The CPU also controls a display to which it is attached. As the user provides inputs through the user input, the display may change. For example, as the buttons are pushed, the display will rotate through a variety of different types of data that may be of interest to the user.

A power supply is connected to the CPU and it is preferably one or more batteries providing a DC power.

To communicate with other computer systems, such as a hospital computer system or a pharmacy computer system, the CPU is attached to a wireless communication module that is also mounted in the cap of the safety shield along with the CPU. In a preferred embodiment, the wireless module communicates by infrared light, but it could also be a wireless radio communications system, another type of wireless communication, or even a wired communication system.

A programmable read only memory is also provided in the cap of the safety shield connected to the CPU. A semi-permanent program is stored within the programmable read only memory along with other data that is repetitively used by the CPU, including its operating system. If any of this semi-permanent data or other information changes, the programmable read only memory may be reprogrammed to include the new data or the new program. More transient data is stored in a read-write memory that is also connected to the CPU. The read-write memory stores information such as the prescription number, a prescription, patient name, workers in a hospital that might be administering the dose, etc. Preferably, the read-write memory is stable and will not lose its memory in the event of a power failure.

The amount of radioactivity contained in the unit-dose syringe is measured initially by a radionuclide dose calibrator and is loaded via wireless IR into the data module. This information is manipulated by programmed logic in the SDS specific for the individual radionuclide's decay characteristics. In this manner, the amount of radioactivity in the contained radionuclide is continually updated and displayed in real-time on the SDS's LCD. Preferably, the data module stores a decay constant for each radionuclide that may be used. The prescription will include the identity of the radionuclide, and using that information, the data module calculates the current amount of radioactivity based on the initial radioactivity, the decay constant, and the decay equation:

a) $A=A_0e^{-\lambda t}$ where $A_0$=initial activity, b) $\lambda$=the decay constant c) t=time, and A=the current activity which is displayed.

Upon receipt of the SDS by the hospital, the dose-specific information in the data module is conveyed by wireless IR to the hospital's RXIS or data management program. In this manner, electronic reconciliation of critical dose information with the user's RxIS or data management systems occurs, all without opening the SDS, or removing the radioactive dose from its shield. While dose data is being read into the user's data system, other information regarding the identity of individuals who may potentially administer the radiopharmaceutical is taken from the user's RxIS or data management program and placed into the SDS data module for later recall and logging.

Figure 29:
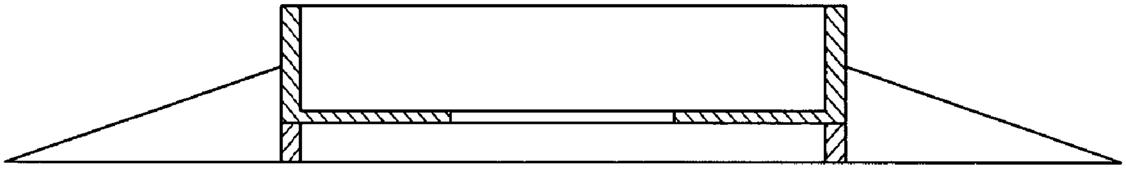
FIG. 29 is a cross sectional view of a base for a canister.

The SafetyDATA Shield—set within a novel slip-fit base (FIG. 29) (which enables stability in the upright position), and a built-in easy-carry bail—contains the patient unit dose all the way from the dispensing pharmacy to the patient's side, without the necessity of opening or further handling of an unshielded dose prior to patient administration. For over-the-road transportation, the SDS is shipped in its matched ORTG transport case, and all ORTG products comply with necessary regulatory guidelines for use and transportation. Referring to FIG. 29, a side cross sectional view of the slip fit base for the canister is shown. In this embodiment, the well of the canister would be circular in a top view and has a diameter of three and one-half inches, which is precisely the diameter of a standard canister. The well lightly grips the bottom of the canister and holds the canister in an upright position. The base is preferably 7½ inches in diameter and also has a circular shape in a top view. The increased diameter of the base as compared to the well creates greater stabilization for holding the canister in an upright position and thereby enables less handling of the canister, which results in less exposure and more convenience. While the preferred dimensions and shapes have been shown, it will be understood that the base diameter, overall height, and well diameter may vary depending upon the application. Also, while a circular base and well is preferred, the base could be other geometric shapes, such as square or polygon shaped cut to sleep. If the canister had a different cross sectional shape, such as a square or polygon cross-section, the well would likewise have a different shape corresponding to the shape of the canister. Therefore, FIG. 29 represents a side cross-section of a base having either a circular or a polygon shape when viewed from the top.

Figure 26:
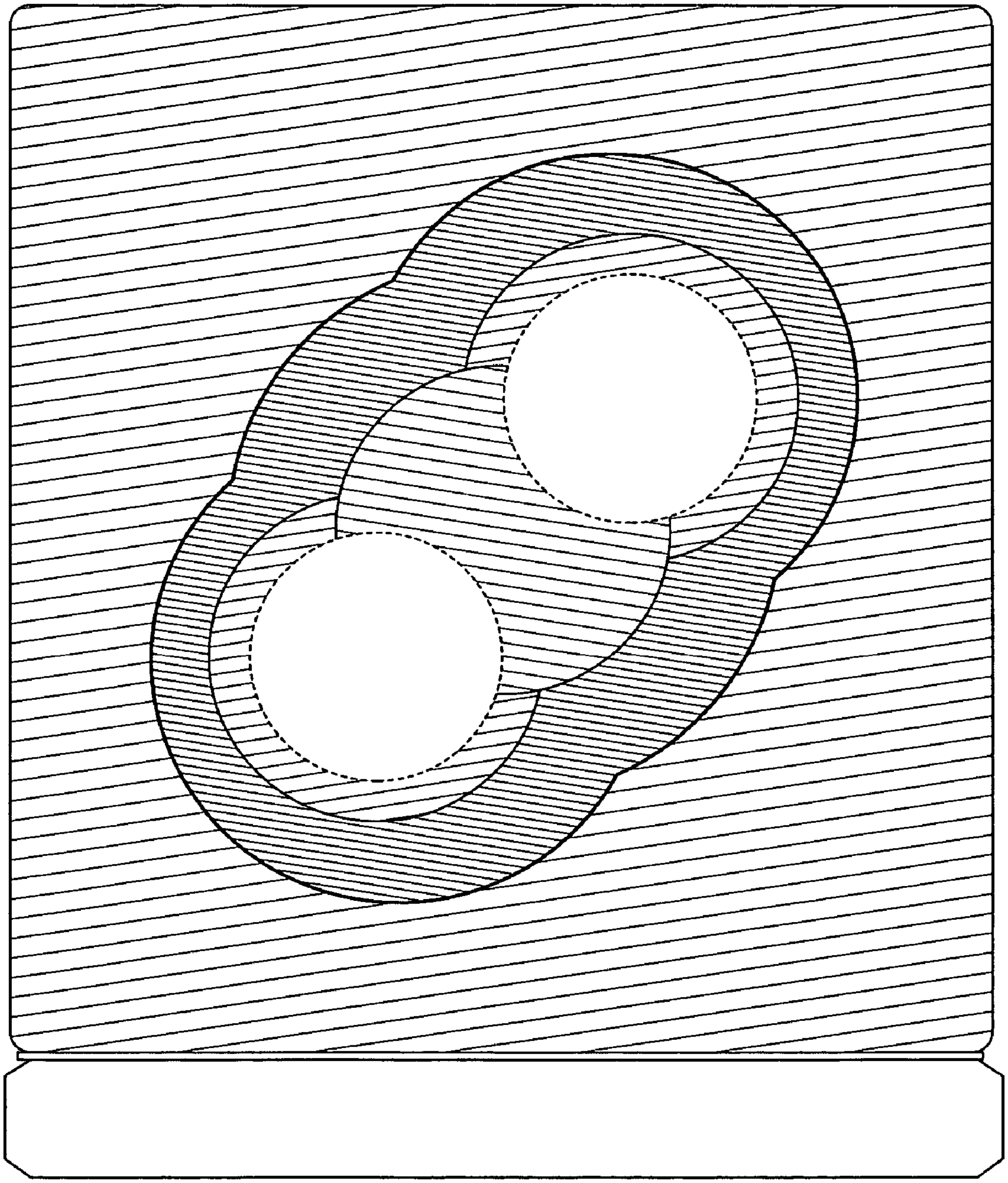
FIG. 26 is a is a top view of a transport case for one, two or three shielding canisters.
Figure 27:
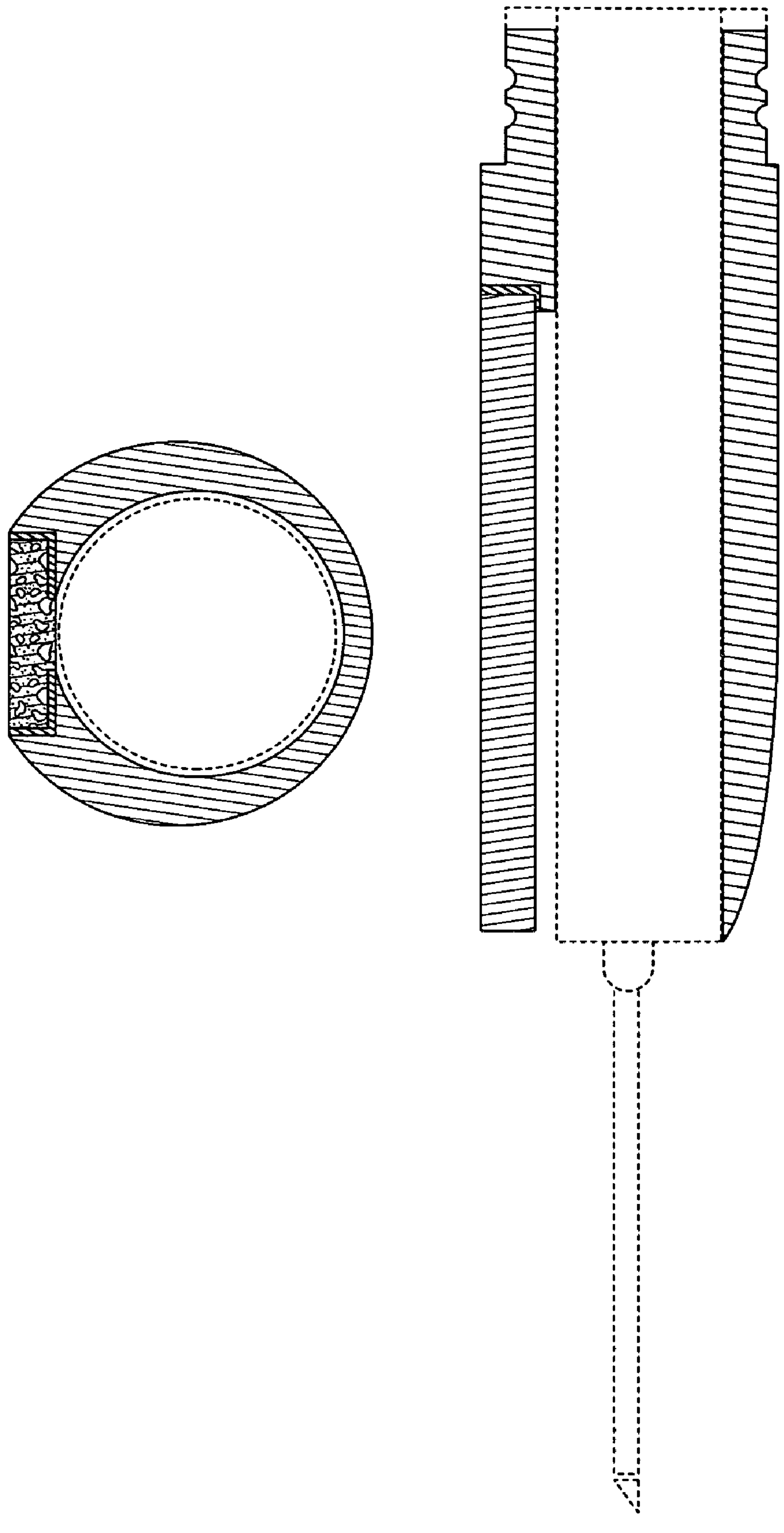
FIG. 27 is a side cross sectional view and a top cross sectional view of a syringe shield.
Figure 28:
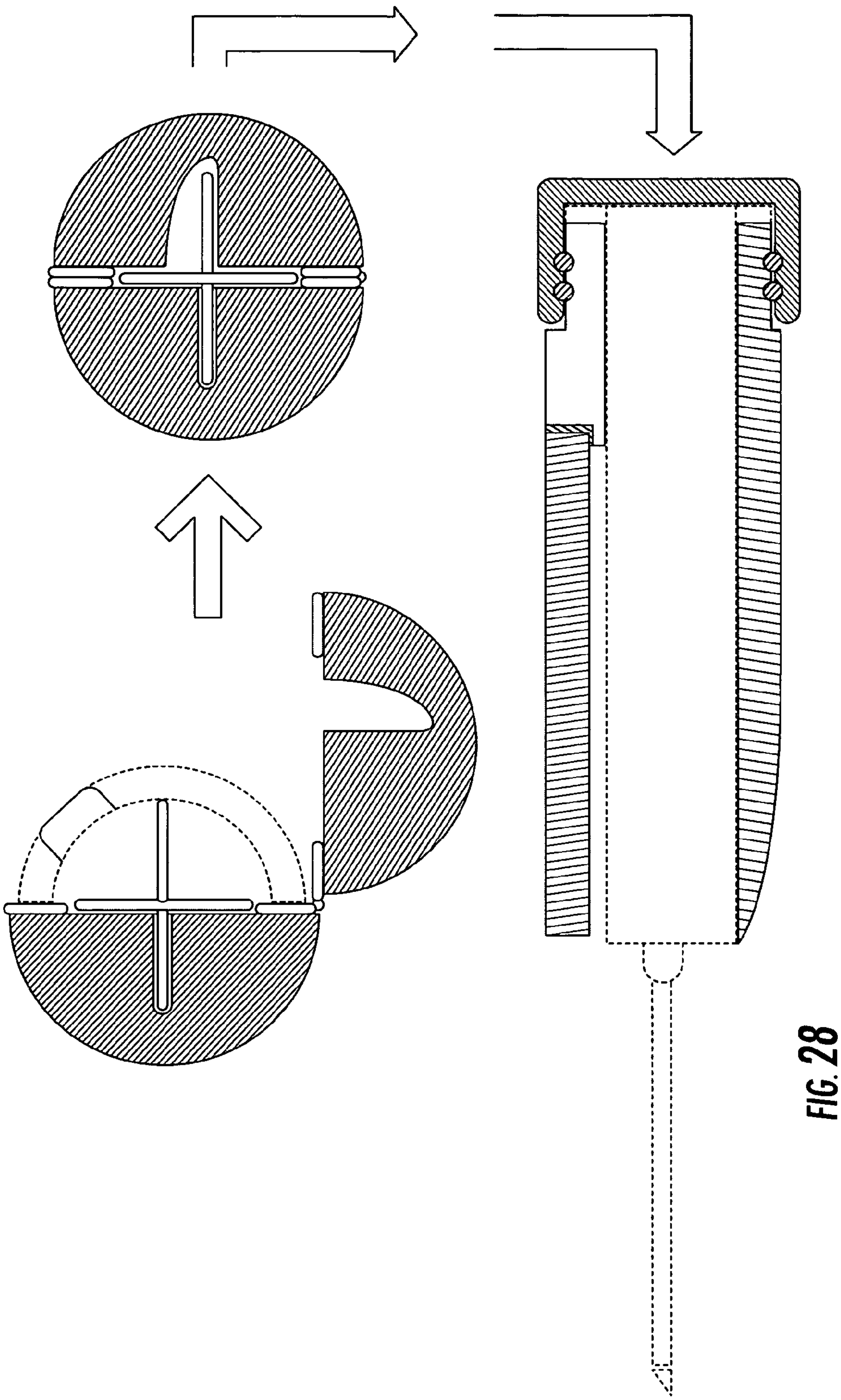
FIG. 28 shows three views of the syringe shield, one showing a longitudinal cross sectional view and two showing end views.

Referring to FIG. 26, a top view of an open transport case is shown. In the this exemplary case, the transport container is square in cross section and includes an outer layer of protective foam, and a radioactive shield is disposed immediately within the outer layer of foam. Within the radioactive shield, a foam socket is provided for carrying one or two canisters (safety shields). When one canister is used, it is placed in the central opening which is configured to hold the canister and prevent it from shifting laterally. If two canisters are being used, they are placed in the openings that are spaced apart on opposite ends of the foam socket. Again, the two outer openings are configured to prevent the canisters from shifting laterally. A lid, which is shown in the open position in FIG. 26, is attached by a hinge to the transport container. Preferably, the lid includes radioactive shielding, such as a lead shield. When the canisters have been inserted into the foam socket, the lid is closed and it is ready for transportation.

Upon opening at the patient's side, a simple turn of the SDS cap (less than ½" rotation) rapidly releases the cap while an internal strut (FIG. 21) ensures that the cap remains attached its matched base such that the unique dose information in the data module and LCD are never separated from the original carrier. The strut prevents contact of the cap with the syringe plunger, thus minimizing spill potential.

A further refinement of the SDS is a specially designed tungsten injection syringe shield (FIGS. 21, 27 and 28) into which the dispensing nuclear pharmacist secures the unit dose syringe before being loaded into the SDS. The tungsten shield, now containing the unit-dose syringe is withdrawn from the SDS only at the desired moment of administration, and acts as a continuously effective personnel shield for the technologist/physician administering the radiopharamceutical. This feature eliminates the need for the technologist/physician to unload a "hot" syringe from a conventional transport/shipping container and insert the syringe into a separate syringe carrier shield at the hospital, or an injection shield at the patient's side. Advantages regarding cumulative personnel exposure are significant.

Upon completing the administration of the radiopharmaceutical, the person performing this task presses in sequence one of the buttons (such as button A in FIG. 22) located on the data module until his/her identity (initials) appears on the LCD, whereupon he/she simultaneously keys both buttons thereby locking in all dose data, including: the time of radiopharmaceutical administration, the precise amount administered, and the identity of the person administrating the drug.

Immediately after injection, the spent syringe, still within the injection shield is returned into the SDS, and the cap is secured onto the base. Before placing the SDS back into the ORTG shield transport container, all electronically 'locked' dosage data is transferred back through the hospital's MIS by wireless IR upload of stored data that links and reconciles the information to its proper location in the user's data RxIS or management program. In this manner, the generation of hand-written, or hard-copy documentation, is no longer required, with all information handled via electronic storage and transfer to similar devices and programs as required to render a final and appropriate record and report.

SDS Models:

The SDS units preferably include four models—A, B, C and D—each designed to appropriately shield radionuclides based upon their critical nuclear properties. Additionally, each model will accommodate either a 3 or 5 cc syringe.

Figure 21:
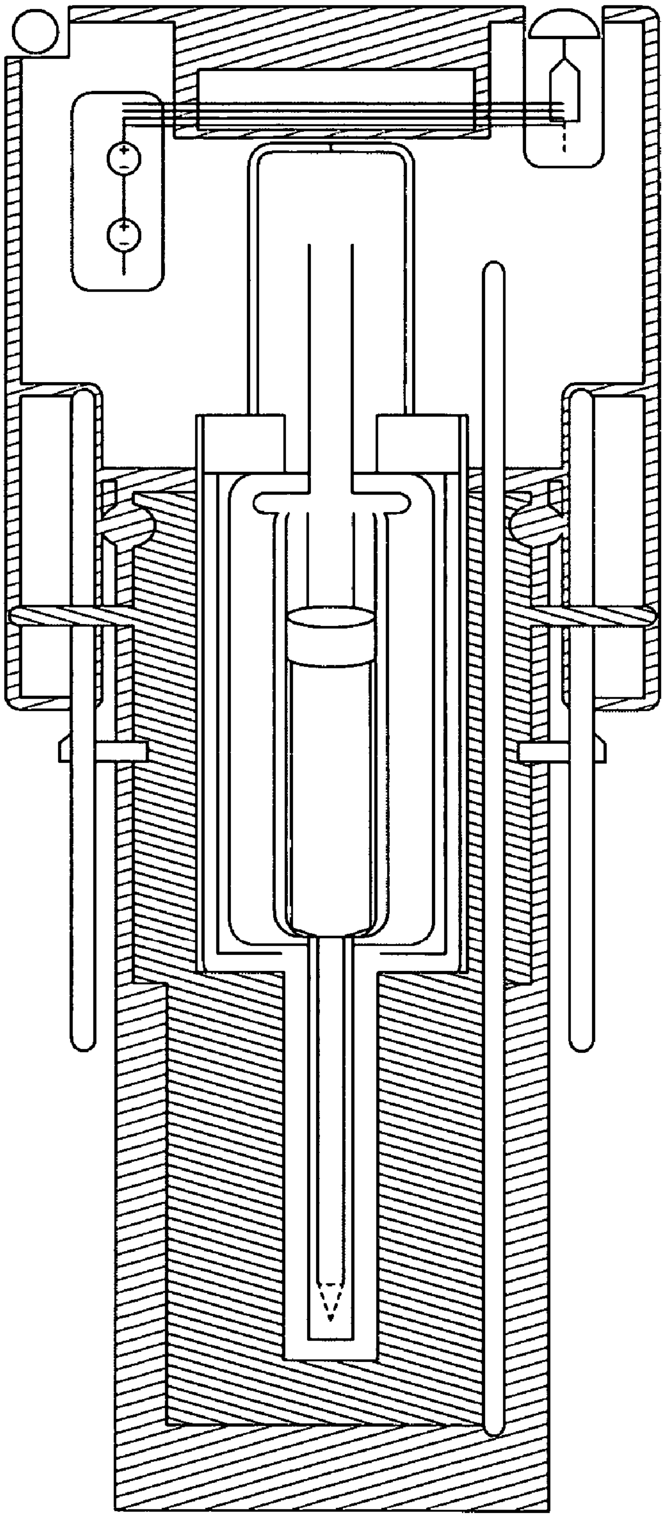
FIG. 21 is a somewhat diagrammatic cross sectional view of a safety data shield, a syringe shield, a syringe, a removable shield cap, and an electronic display device mounted in the cap.
Figure 23:
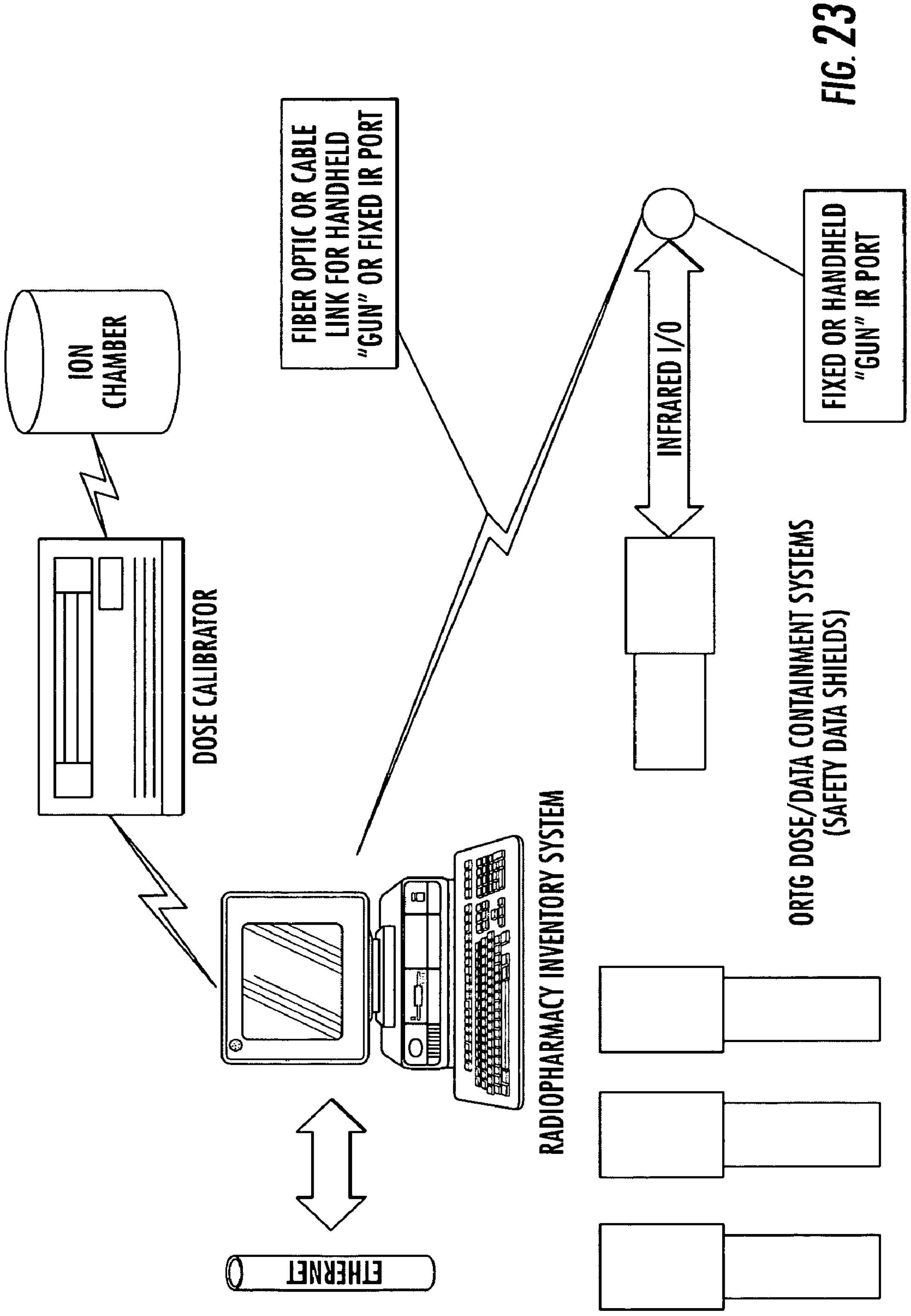
FIG. 23 is a diagram of a system for dispensing and distributing radioactive medicine.

The SDS is Represented in FIGS. 21-23.

Model A—to safely shield and contain a variety of radionuclides and radiopharmaceuticals including mostly Tc-99m and Tl-201, with gamma energies not greater than approximately 165 keV.

Shielding Design Specifications:

Material Construction: Tungsten syringe shield/Lead containment combo

Transport Container Shielding to meet appropriate state and/or federal (or other) regulations for transportation

| Radionuclide | Maximum Activity | Containment Surface Reading | Lead Containment Thickness | Tungsten Syringe Shield Thickness |
|---|---|---|---|---|
| Technetium-99m Thallium-201 | 50 mCi | <19 mR/hr | 0.2 cm | 0.2 cm |

[Other specifications TBA]

Model B—to safely shield radiopharmaceuticals including Ga-67, In-111, and I-131 (in amounts not to exceed 20 mCi) and other gamma emitting radiopharmaceuticals with energies not greater than 375 keV.

Shielding Specifications

Material Construction: Tungsten/Lead syringe shield/Lead containment combo

| Radionuclide | Maximum Activity | Containment Surface Reading | Lead Containment Thickness | Tungsten/Lead Syringe Shield Thickness |
|---|---|---|---|---|
| Gallium-67 Indium-111 Iodine-131 | 20 mCi | <670 mR/hr | 1.5 cm | 0.2 + 0.3 = 0.5 cm |

Transport Container Shielding to meet appropriate state and/or federal (or other) regulations for transportation Model C—to safely shield positron-emitting radiopharmaceuticals, I-131 in amounts employed for radiotherapy, and other beta and gamma-emitting radiopharmaceuticals employed for therapeutic applications.

Shielding Design Specifications

Material Construction: Tungsten/Lead combo

Transport Container Shielding to meet appropriate state and/or federal (or other) regulations for transportation

[Other specifications TBA]

| Radionuclide | Maximum Activity | Containment Surface Reading | Lead Containment Thickness | Tungsten/Lead Syringe Shield Thickness |
|---|---|---|---|---|
| Fluorine-18 Iodine-131 Strontium-89 | 400 mCi | <120 mR/hr | 1.25 cm | 0.2 + 0.6 = 0.8 cm |

Model D—to safely shield $\beta^+$ emitting radiopharmaceuticals (without gamma emissions) that are employed for therapeutic applications.

Shielding Specifications

Material construction: Lead/Lucite combo

[Other specifications TBA]

| Radionuclide | Maximum Activity | Surface Reading | Lucite Thickness |
|---|---|---|---|
| Phosphorous-32 | | | |

SDS Uniform Design Elements:

A: External Surface and Appearance: All external surfaces will be constructed of seamless brushed aluminum, or other suitable material—hardness and thickness based on configuration of internal lead or tungsten shielding material specific to the emitters contained within. The internal lead or tungsten shielding is designed to meet or exceed all regulatory requirements. Non-permeable surface suitable for use with cleaning solutions, including disinfectants and decontamination solutions. A quick-release locking and unlocking mechanism significantly minimizes hand exposure (no threads). An integrated rail system for top and bottom of the canister to maintain inventory integrity and minimize risk management scenarios. Integral "bail" handle allows convenient handling and transport of the SDS, then stores out of way during shipping and use. For additional on-site stability in the upright position, the SDS is inserted, via slip-fit, into wide-stance plastic base that can be custom labeled to display radiopharmacy logo (FIG. 29).

B. Internal surface: All internal surfaces will be either epoxy over lead or brushed tungsten. Non-permeable. Plastic (nylon) cylinder spacers will be used to accommodate a 3 cc-syringe shield within the bore necessary to retain a 5 cc-syringe shield.

C. Syringe Shield: Tungsten syringe shield in both 3 cc and 5 cc sizes to include leaded sight glass (5.2 g Pb/cc) to visualize syringe contents. Syringe shield and syringe flange latch to include twist lock mechanism to rapidly secure syringe shield to loaded syringe designed to tolerances for a specific syringe manufacturer.

D. Seals and O-rings: With the locking mechanism engaged, the cap and base are securely joined against a compression-spring with the cap simultaneously nested against an embedded O-ring in the SDS collar, all sufficient to contain the internal contents of the SDS, protect the contents against external contamination, and against pressure gradient changes.

E. Regulatory Testing and Certifications: The SDS will meet all applicable requirements of the US Department of Transportation for transportation of radioactive materials, and other regulatory guidelines as appropriate.

The SDS Data Display Device

The Data Display Device (DDD) will be an integral part of each SafetyDATA Shield, to be configured as pictured in FIGS. 21 and 22.

Each DDD will consist of:

A. Microprocessor with internal clock and program function. Encoding of information matching microprocessor to container serial number to minimize tamper potential and measures to prevent unauthorized software modifications.

B. 2-line LCD display that scrolls stored and computed information in a continuous fashion or by the paging function of the pushbuttons.

C. Power source.

D. Wireless input/output module to enable reception of data transmission (download function) and transfer of locked information (upload function). Methodology described herein involves Infra-Red technology, but may involve other technologies to include RF and OCR. Wired communication is an optional embodiment.

E. Input buttons used to page memory for display and lock dosage information upon administration.

F. Sufficient sealing and shock mounting to maintain non-permeability specifications of SDS and immunity to hazards anticipated to be encountered during routine use.

A. Microprocessor

TBA

B. LCD Component

The LCD will be located on the top of the cap of the SDS, as shown below, and will display one or two lines of data, cycling between data sets. The cycling will be overridden with the operator's activation of one of the buttons, also located on the top of the unit to allow memory registers to be paged to display, and with appropriate keystrokes, lock selected data for subsequent upload.

Power Source

The microprocessor, LCD, and Wireless Infra-Red components will be powered by an internal power source.

Wireless (InfraRed) Transceivers

In one embodiment, separate IR receiver and transmitter components will be utilized. Low-drain receiver will monitor environment for encoded signal to enable a receive or to request a transmit from the SDS.

ORTG Wireless [IR] Transceiver and Interface

Operational Configuration of the SDS, RxIS, IR Interface and Dose Calibrator is pictured in FIG. 23. At the dispensing nuclear pharmacy, a signal registering the quantity of the radionuclide measurement is obtained by the radionuclide dose calibrator and is forwarded into the Rx information system (RxIS), whereupon the following information is acquired by the ORTG microprocessor via wireless (IR) link:

Patient identity

Hospital identity

Radiopharmaceutical name

Amount of activity in unit dose

The composite information is stored within the Rx information system (RxIS), then transmitted by wireless (IR) interface to the SDS unit into which the unit dose syringe has been placed. The interface is connected to a COM or Serial port on the RxIS and cabling allows for a "beam gun" configuration to minimize contact between personnel and the SDS, thereby further minimizing radiation dose. Wireless options include transmission by RF, character recognition and storage, or other wireless options from the interface to the SDS. A wired option may also be used.

Comparison Between Current Technology and Use of the ORTG SDS

Figure 24:
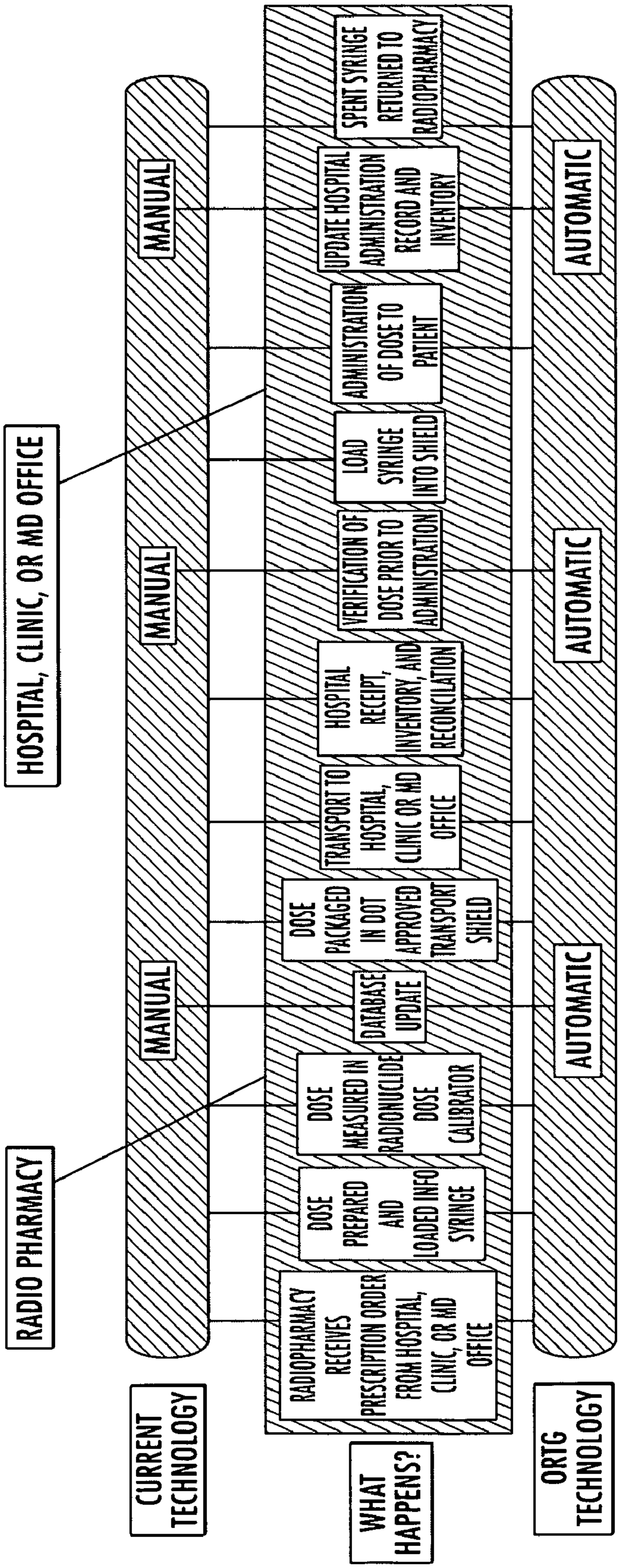
FIG. 24 is a diagram illustrating the flow of a radioactive dose from a pharmacy to a patient and back to the pharmacy and comparing the current invention to current technology.

A pictorial comparison between current technology and ORTG Technology is depicted in FIG. 24.

The use of the SDS will significantly reduce personnel radiation exposure while minimizing record and clerical error. Additionally, steps currently required in the management and handling of radioactive materials from the radiopharmacy to the patient are minimized or eliminated, resulting in significant efficiencies. All scenarios result in risk management reduction and are consistent with As Low As Reasonably Achievable (ALARA) requirements for the reduction in radiation exposure. Consequently, radiation exposures that currently result in the potential for restricting personnel activity due to overexposure are minimized, thus increasing the efficacy and productivity of personnel.

Referring to FIG. 24, the top horizontal bar represents current technology and the bottom horizontal bar represents the technology of the present invention. As described above, the current technology usually requires the manual transfer of information, such as by writing on labels, to transfer information from the pharmacy to the hospital, clinic or doctor's office. As shown in FIG. 24, after a dose is measured in the dose calibrator (activity measurement device), it is necessary to indicate the activity of the dose so that it may be used later by other health care professionals. Using current technology, the dose activity would be written manually on a label, or a future activity level at a particular time may be written on the label, and the label is applied to the syringe or its carrier. Using the safety shield of the present invention, the needed data is loaded into the data module automatically as indicated by the first automatic button on the lower horizontal bar.

As indicated by the second automatic button on the lower bar, the transfer of information at the hospital is likewise automatic. That is, the data module of the safety shield communicates wirelessly with the computer system at the hospital and provides the needed information concerning the patient, the prescription, the original radioactivity (optional), the current activity, and similar information. At the same time, the hospital computer system will communicate to the data module of the safety shield certain the needed information, such as the initials and names of the health care professionals that may be caring for this particular patient.

Also as indicated in FIG. 24, the verification of dose prior to administration is automatic. In other words, the data module of the safety shield is constantly calculating the current activity of the dose. Therefore, the health care professional can check the current activity against the prescribed activity immediately prior to administering the dose to the patient. It will be recalled that the prescription is contained in the data module as well as the current activity of the dose. Thus, the comparison between two activities can be accomplished by simply scrolling through the information provided by the data module. It is not necessary to calculate a current dosage activity based on the original dose, or calculate a current dosage activity for the time at which the dose was actually administered based on a calculated activity for the dose at the time the dose was originally intended to be administered.

In FIG. 24, the step "Load Syringe Into Shield" is shown as a manual step in current technology, but no such step is shown in the technology of the present invention. Because the syringe is already loaded in a syringe shield within the safety shield, it is not necessary to manually load the syringe into a separate shield prior to handling the syringe and administering the dose to the patient.

The step identified in FIG. 24 as "Update Hospital Administration Record And Inventory" is shown as manual in the current technology but automatic with the technology of the present invention. Again, this indicates that it is not necessary to manually type information into the hospital records after the dose has been administered. Instead, the data module of the safety shield is placed into communication, preferably wireless communication, with the hospital computer system and all relevant information is transferred to the hospital computer system, including the name of the patient, and the prescription, the activity of the dose when administered to the patient, the time of administration of the dose, and the medical personnel involved in the procedure.

When the syringe is removed from the safety shield and when the syringe is returned to the safety shield, some exposure to the health care professionals may result even though the dose is continuously shielded. To further minimize exposure, a quick release cap is provided so that the syringe may be removed from the shield in a minimum amount of time. Also, while the cap is being removed, the shield may be positioned in its base so that it is not actually necessary to grip the shield while the cap is being removed or the cap is being replaced onto the bottom of the canister. In prior art devices, it was often necessary for health care professionals to hold canisters and painstakingly unscrew the cap from the bottom of the canister. This unnecessary holding of the canister represents an unnecessary exposure of health-care professionals to some amount of radioactivity.

Detailed Data Characteristics in ORTG Systems

The table below provides the detailed characteristics of the above described system. It is believed that the table is self-explanatory, so only a brief explanation is provided herein. The table shows a particular location and at each location details of the activity performed by the data module of the safety shield are shown. The table is shown with the locations in the order in which the radioactive dose progresses from the pharmacy to the hospital, to the patient and back to the pharmacy. The column labeled "Data Channel" describes the types of information that are being transferred between the data module and another computer system. The last location is shown as "Updated?". This location represents a maintenance location in which information is being updated by the operator under circumstances other than the typical operating conditions where a radioactive dose is being delivered to a patient and returned.

| Location | Data | RxIS | Dose Calib | ORTG SDS |
|---|---|---|---|---|
| Pharmacy | Wake Up | I/O State | Pass Through | IR to I/O State |
| | End Self Check State | Pharmacy Load | Pass Through | Stored/Verified |
| | SDS S/N | Stored | Pass Through | Readback |
| | SDS Memory State | Verified | Pass Through | Readback |
| | SDS Battery State | Verified | Pass Through | Readback |
| | Abort Load if Error | Verified | Pass Through | Error Display |
| | Pre vs. Post Dose S/N | Reconcile/Verified | | |
| | Patient Name | Pharmacy Load | Pass Through | Stored/Verified |
| | Rx Number | Pharmacy Load | Pass Through | Stored/Verified |
| | Radionuclide + Chem. Form | Pharmacy Load | Entered/Verified | Stored/Verified |
| | Decay Factor | | Pharmacy Load | Stored/Verified |
| | (option) | Pharmacy Load | Pass Through | Stored/Verified |

-continued

| Location | Data | RxIS | Dose Calib | ORTG SDS |
|---|---|---|---|---|
| | Chemical Form | Pharmacy Load | Pass Through | Stored/Verified |
| | (option) | | Pharmacy Load | Stored/Verified |
| | Assay (in uCi) | Dose Calibrator | Pharmacy Load | Stored/Verified |
| | Client/Hospital | Pharmacy Load | Pass Through | Stored/Verified |
| | GMT | Stored/Verified | Pass Through | Stored/Verified |
| | Client Time Zone | Pharmacy Load | Pass Through | Stored/Verified |
| | Rx Expiration Time | Pharmacy Load | Pass Through | Stored/Verified |
| | Future Use | Null | Null | Null |
| | Future Use | Null | Null | Null |
| | SDS Data Verification | Verified | Pass Through | Readback |
| Hospital Lab | Wake Up | I/O State | Pass Through | IR to I/O State |
| | SDS S/N | Verified/Inventory | Pass Through | Readback |
| | Pre vs Post Dose S/N | Reconcile/Verified | | |
| | Patient Name | Verified/Inventory | Pass Through | Readback |
| | Reset Name | Hospital Load | Pass Through | Stored/Verified |
| | Rx Number | Verified/Inventory | Pass Through | Readback |
| | Rx Number Amend | Hospital Load | Pass Through | Stored/Verified |
| | Pt/Rx # Reset? | Hospital Load | Pass Through | Stored/Verified |
| | Radionuclide | Verified/Inventory | Pass Through | Readback |
| | Chemical Form | Verified/Inventory | Pass Through | Readback |
| | Assay (in uCi) | Verified/Inventory | Pass Through | Readback |
| | Client/Hospital | Verified/Inventory | Pass Through | Readback |
| | GMT | Verified/Inventory | Pass Through | Readback |
| | Client Time Zone | Verified/Inventory | Pass Through | Readback |
| | Rx Expiration Time | Verified/Inventory | Pass Through | Readback |
| | Technologist Ledger | Hospital Load | Pass Through | Stored/Verified |
| | Future Use | Null | Null | Null |
| | Future Use | Null | Null | Null |
| | SDS Battery State | Verified/Inventory | Pass Through | Readback |
| | SDS Data Verification | Verified/Inventory | Pass Through | Readback |
| Patient Area | Patient Name | | | Locked |
| | Rx Number | | | Locked |
| | Pt/Rx # Reset? | | | Locked |
| | Radionuclide | | | Locked |
| | Chemical Form | | | Locked |
| | Assay (in uCi) | | | Lock Realtime |
| | Client/Hospital | | | Locked |
| | GMT | | | Lock Realtime |
| | Client Time Zone | | | Locked |
| | Rx Expiration Time | | | Locked |
| | Technologist Ledger | | | Lock Selection |
| | Future Use | Null | Null | Null |
| | Future Use | Null | Null | Null |
| | SDS S/N | | | Locked |
| Hospital Lab | Wake Up | I/O State | Pass Through | IR to I/O State |
| | SDS S/N | Inventory/Archive | Pass Through | Locked Read |
| | Pre vs Post Dose S/N | Reconcile/Verified | | |
| | Patient Name | Inventory/Archive | Pass Through | Locked Read |
| | Rx Number | Inventory/Archive | Pass Through | Locked Read |
| | Pt/Rx # Reset? | Inventory/Archive | Pass Through | Locked Read |
| | Radionuclide | Inventory/Archive | Pass Through | Locked Read |
| | Chemical Form | Inventory/Archive | Pass Through | Locked Read |
| | Locked Assay | Inventory/Archive | Pass Through | Locked Read |
| | Client/Hospital | Inventory/Archive | Pass Through | Locked Read |
| | Locked GMT | Inventory/Archive | Pass Through | Locked Read |
| | Client Time Zone | Inventory/Archive | Pass Through | Locked Read |
| | Rx Expiration Time | Inventory/Archive | Pass Through | Locked Read |
| | Locked Technologist | Inventory/Archive | Pass Through | Locked Read |
| | Future Use | Null | Null | Null |
| | Future Use | Null | Null | Null |
| | SDS Battery State | Inventory/Archive | Pass Through | Readout |
| | SDS Data Verification | Inventory/Archive | Pass Through | Readout |
| Pharmacy | Wake Up | I/O State | Pass Through | IR to I/O State |
| | SDS S/N | Inventory/Archive | Pass Through | Locked Read |
| | Pre vs Post Dose S/N | Reconcile/Verified | | |
| | Patient Name | Inventory/Archive | Pass Through | Locked Read |
| | Rx Number | Inventory/Archive | Pass Through | Locked Read |
| | Pt/Rx # Reset? | Inventory/Archive | Pass Through | Locked Read |
| | Radionuclide | Inventory/Archive | Pass Through | Locked Read |
| | Chemical Form | Inventory/Archive | Pass Through | Locked Read |
| | Locked Assay | Inventory/Archive | Pass Through | Locked Read |
| | Client/Hospital | Inventory/Archive | Pass Through | Locked Read |
| | Locked GMT | Inventory/Archive | Pass Through | Locked Read |
| | Client Time Zone | Inventory/Archive | Pass Through | Locked Read |
| | Rx Expiration Time | Inventory/Archive | Pass Through | Locked Read |
| | Locked Technologist | Inventory/Archive | Pass Through | Locked Read |
| | Future Use | Null | Null | Null |

-continued

| Location | Data | RxIS | Dose Calib | ORTG SDS |
|---|---|---|---|---|
| | Future Use | Null | Null | Null |
| | SDS Battery State | Inventory/Archive | Pass Through | Readout |
| | SDS Data Verification | Inventory/Archive | Pass Through | Readout |
| | Clear Data | | | Initiate |
| | Self Check State | | | Initiate |

| Updated? | Data Channel | Units | Alpha or Numeric | Characters | Alternate | Display Format |
|---|---|---|---|---|---|---|
| No | SDS S/N | | Both (A, N) | | 12protected mode | in ROM |
| reset only | Patient Name | | Alpha (A) | | 12 | Last, First Truncated at 12 digits |
| reset only | Rx Number | | Both (A, N) | | 12 | Rx (9 digits) |
| reset only | Pt/Rx # Reset | True/False | | never displayed | | |
| No | Radionuclide | | Both (A, N) | | 12 | AA-NNNA (A-NNN, AA-NN, etc) |
| No | Decay Factor | log | Numeric (N) | never displayed | | |
| No | Chemical Form | | Alpha (A) | | 12 | Alpha Truncated at 12 Digits |
| q 6 sec. | Assay/Locked Assay | uCi | Both (A, N) | xxxxxx.xxuCi | computed | xxx.xx uCi [or xxx.xx mCi] |
| No | Client/Hospital | | Both (A, N) | | 12 | Alpha Truncated at 12 Digits |
| TBA | GMT/Locked GMT | hh.mm.s | | never displayed | | |
| No | Client Time Zone | integer | | never displayed | | |
| q 6 sec. | Local Time/Locked Time | hh.mm | Both (A, N) | | 12computed? | local hh.mm (option military time?) |
| No | Rx Expiration Time | hh.mm | Both (A, N) | | 12 | RxExp hh.mm (Rx Expired Status) |
| q 6 sec. | Rx Expired | | internal compare Rx Expiration Time with Local Time | | | [Display if Expired Only] |
| No | Technologist Ledger | | Alpha (A) | ? | Initials? | [Display when called at bedside lock] |
| Lock state | Locked Technologist | | Alpha (A) | | 12 | Admin by AAA |
| IFF fault | Fault Code | | Numeric (N) | | 12 | Never displayed if normal |

SUMMARY OF SDS OPERATION AND DATA TRANSFER

The Safety Data Shield may store:

Safety Data Shield S/N
Patient Name
Rx Number
Prescription
Radionuclide
Decay Factor
Chemical Form
Activity Level
Client/Hospital
Local Time
Rx Expiration Time
Technologist Initials The Safety Data Shield Will Display Patient Name
Radionuclide Activity Level
Rx Number
Prescription
Client/Hospital
Local Time
Technologist Initials
Expired, if Rx time has expired When dose is administered to patient and information is uploaded to hospital's MIS, display will indicate Spent.

When dose has expired and this information is uploaded to MIS, the display will indicate Expired.

When dose has not been used and this information has been uploaded to the MIS, the display will indicate Not Used.

Spent and Not Used will always override Expired

A normal sequence of operation for the Safety Data Shield is as follows:

Pharmacy

Clear memory if not already cleared
Perform self check on memory
Load memory with data
 Safety Data Shield S/N
Dose S/N
Patient Name
Rx Number
Radionuclide
Decay Factor
Chemical Form
Activity in uCi
Client/Hospital
GMT
Client local time
Rx Expiration date Any errors will return shield to first step Hospital "Hot" Lab All memory data is uploaded to Hospital's RxIS or Management Information System. In addition, Technologist Ledger is downloaded to Safety Data Shield Patient Administration Area Check current radionuclide activity level and administer dose.

When dose has been administered, the Technologist will lock in memory his/her initials along with the time and radionuclide activity.

Hospital "Hot" Lab

All memory data is uploaded to Hospital's RxIS. When information has been verified, The Safety Data Shield memory is cleared and the display will indicate data has been transmitted and memory is otherwise "cleared" for future use.

The Safety Data Shield is returned to Pharmacy for reuse.

What is claimed is:

1. A shielded radioactive medical apparatus for use in medical treatments requiring radioactive objects, the apparatus comprising:

a single tubular housing including a closed end and an open end, a plurality of bores located proximate the open end, a plurality of pins located within the plurality of bores, and a plurality of springs engaged with the plurality of pins for outwardly biasing the plurality of pins;

a quick release cap having a distal end and a proximate end, the proximate end configured for closing the open end of the tubular housing wherein the proximate end includes a receiver, and a quick release mechanism configured for engaging and holding the quick release cap on the open end of the tubular housing and quickly releasing the quick release cap when actuated by a user, the quick release mechanism including a collar movably engaged along the open end of the tubular housing, the collar including a first end and a second end, wherein the first end includes an inclined engagement surface;

a biasing member engaged with the collar to bias the collar in a direction substantially away from the closed end of the tubular housing;

wherein the quick release cap may be rapidly engaged with the tubular housing by inserting the proximate end of the cap within the collar so that the plurality of pins are urged inward in the plurality of bores as the pins slide along the inclined engagement surface of the first end of the collar and the plurality of pins engage with the receiver, thereby substantially locking the quick release cap onto the tubular housing; and wherein the quick release cap may be rapidly removed from the tubular housing by moving the collar toward the closed end of the tubular housing so that the plurality of pins are no longer urged into the plurality of bores and engaged with the receiver, thereby substantially freeing the quick release cap from the tubular housing.

2. The apparatus of claim 1 further comprising:

a lower radioactive shield located within the tubular housing and an upper radioactive shield located within the quick release cap.

3. The apparatus of claim 1 further comprising a keyed rail including a key, the keyed rail extending from and attached to the proximate end of the quick release cap;

wherein the quick release cap further comprises a rail cavity, and wherein the housing further comprises a slotted cavity including a slot along the length of the slotted cavity, and a cutout proximate the open end of the housing, and an opening located along the open end of the housing including a guide bearing located in the opening, wherein the keyed rail is slidably located on the guide bearing along the slotted cavity of the housing, and wherein the key may be mated with the slot in the cavity, thereby allowing the cap to be moved away from the housing while not allowing the cap to rotate about the rail.

4. The apparatus of claim 1 wherein the cap further comprises a plurality of substantially planar surfaces, wherein the housing includes a plurality of extensions, and wherein the apparatus further comprises a flip top arm attached to at least two of the level surfaces, the flip top arm including a pair of slots, each slot including an angled portion along an end of the slot closest to the cap, wherein at least two of the plurality of extensions are located within the slots, whereby the cap may be rapidly removed along a path defined by the movement of the flip top arm along the extensions.

5. A shielded medical apparatus for use in medical treatments requiring radioactive objects, the apparatus comprising:

a single tubular housing including a closed end and an open end, a plurality of bores located proximate the open end, a plurality of balls located within the plurality of bores, and a plurality of springs engaged with the plurality of balls for outwardly biasing the plurality of balls;

a quick release cap having a distal end and a proximate end, the proximate end configured for closing the open end of the tubular housing wherein the proximate end includes a receiver, and a quick release mechanism configured for engaging and holding the quick release cap on the open end of the tubular housing and quickly releasing the quick release cap when actuated by a user, the quick release mechanism including a collar movably engaged along the open end of the tubular housing, the collar including a first end and a second end, wherein the first end includes an inclined engagement surface; and a biasing member engaged with the collar to bias the collar in a direction substantially away from the closed end of the tubular housing;

wherein the quick release cap may be rapidly engaged with the tubular housing by inserting the proximate end of the cap within the collar so that the plurality of balls are urged inward in the plurality of bores as the balls advance along the inclined engagement surface of the first end of the collar and the plurality of balls engage with the receiver, thereby substantially locking the quick release cap onto the tubular housing; and wherein the quick release cap may be rapidly removed from the tubular housing by moving the collar toward the closed end of the tubular housing so that the plurality of balls are no longer urged into the plurality of bores and engaged with the receiver, thereby substantially freeing the quick release cap from the tubular housing.

* * * * *